United States Patent
Shah et al.

(10) Patent No.: US 12,115,270 B2
(45) Date of Patent: Oct. 15, 2024

(54) PULSED XENON ULTRAVIOLET (UV) DISINFECTION SYSTEM

(71) Applicant: HELIOSXE TECHNOLOGIES INC., Milford, NH (US)

(72) Inventors: Pratik Shah, Guelph (CA); Vinay Sreekumar, Fresno, CA (US); Vinod Menon, Merrimack, NH (US)

(73) Assignee: HELIOSXE TECHNOLOGIES INC., Milford, NH (US)

( * ) Notice: Subject to any disclaimer, the term of this patent is extended or adjusted under 35 U.S.C. 154(b) by 503 days.

(21) Appl. No.: 17/400,848

(22) Filed: Aug. 12, 2021

(65) Prior Publication Data

US 2022/0047738 A1  Feb. 17, 2022

Related U.S. Application Data

(60) Provisional application No. 63/065,158, filed on Aug. 13, 2020.

(51) Int. Cl.
*A61L 2/10* (2006.01)

(52) U.S. Cl.
CPC .............. *A61L 2/10* (2013.01); *A61L 2202/11* (2013.01); *A61L 2202/121* (2013.01); *A61L 2202/14* (2013.01); *A61L 2202/16* (2013.01)

(58) Field of Classification Search
CPC ................... A61L 2/10; A61L 2202/11; A61L 2202/121; A61L 2202/14; A61L 2202/16; A61L 2202/25; A61L 9/20
See application file for complete search history.

(56) References Cited

U.S. PATENT DOCUMENTS

| | | | | |
|---|---|---|---|---|
| 6,028,315 A * | 2/2000 | Bailey | ..................... | A61L 2/10 250/455.11 |
| 9,370,600 B1 * | 6/2016 | DuPuis | ................... | F21V 14/08 |
| 11,511,007 B2 * | 11/2022 | Stibich | ................... | G16H 40/20 |
| 2003/0030015 A1 * | 2/2003 | Waluszko | ................. | A61L 2/10 250/503.1 |
| 2016/0296649 A1 * | 10/2016 | Ramanand | ................ | A61L 2/10 |
| 2021/0299295 A1 * | 9/2021 | Rubaek | ...................... | A61L 2/24 |
| 2021/0370826 A1 * | 12/2021 | Umenei | .................. | G06F 3/041 |
| 2022/0047738 A1 * | 2/2022 | Shah | ......................... | A61L 2/10 |
| 2023/0330292 A1 * | 10/2023 | Cristofaro | ............. | G07F 19/201 |

* cited by examiner

*Primary Examiner* — David A Vanore

(74) *Attorney, Agent, or Firm* — Oliff PLC

(57) ABSTRACT

A pulsed xenon UV disinfection system for treating objects present inside a room and/or area surrounding the system. The system includes an head portion, an intermediate portion and a lower portion. The head portion includes a lamp, a housing and a reflector to redirect the UV rays in preferred direction. A shutter mechanism is disposed in the intermediate portion includes a shutter to provide protection to the lamp. A shape changing mechanism comprising second actuator to change shape of reflector as per the treatment conditions and/or physical characteristics of the room. The shape of reflector facilitates to converge or diverge UV rays emitted by the lamp to effectively treat objects/area close to the system or away from the system, respectively.

20 Claims, 13 Drawing Sheets

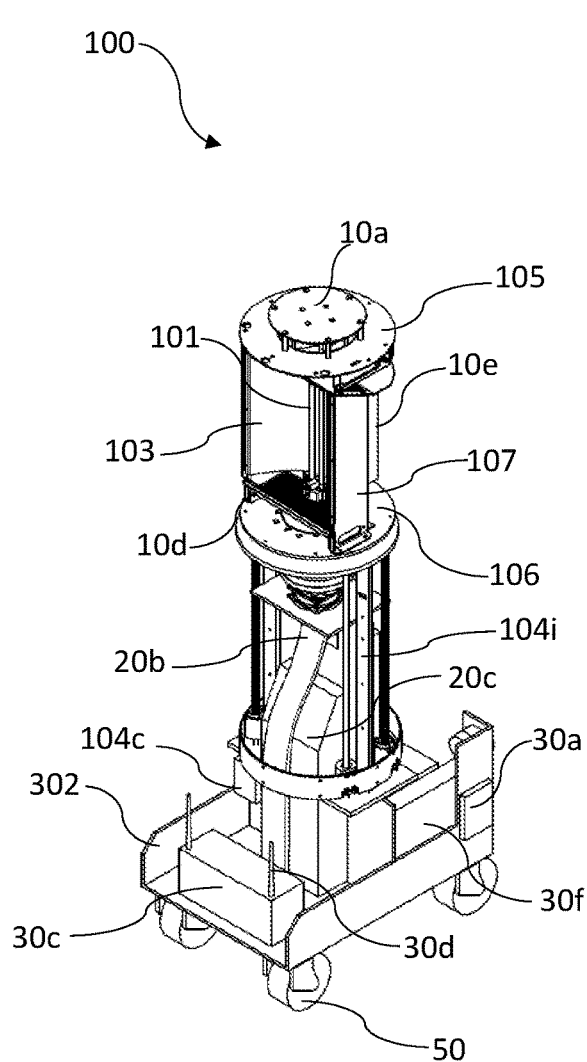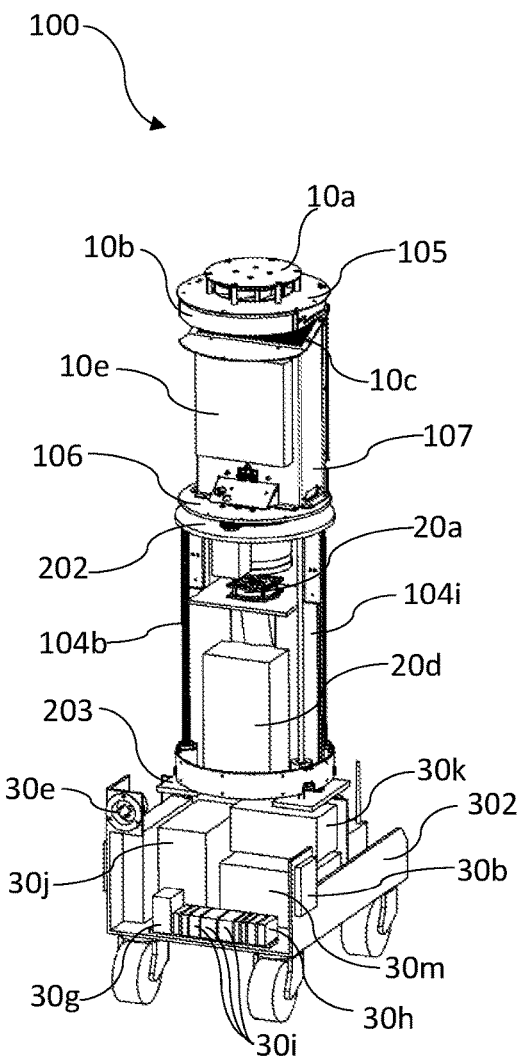
Fig. 4
Fig. 5

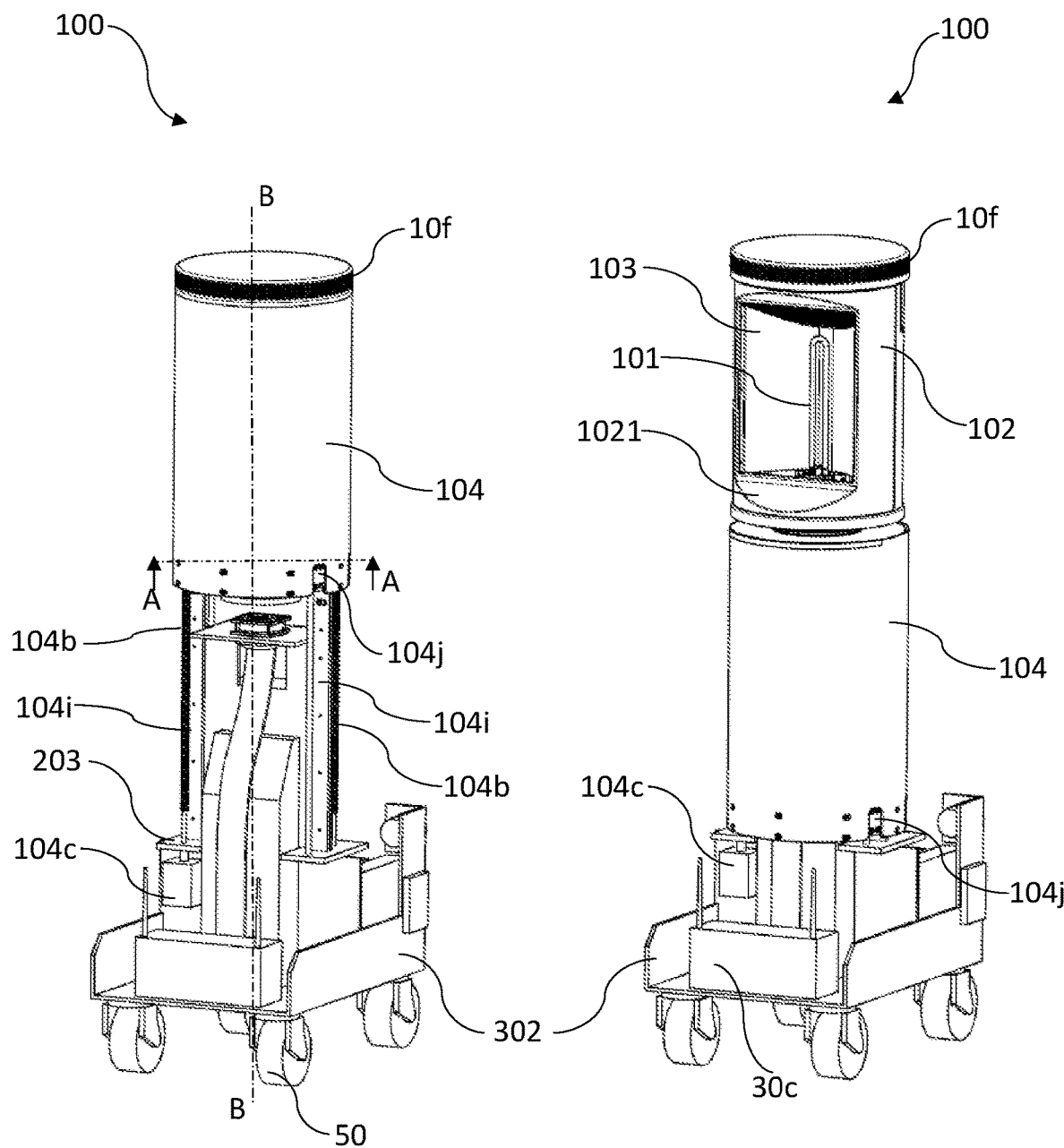

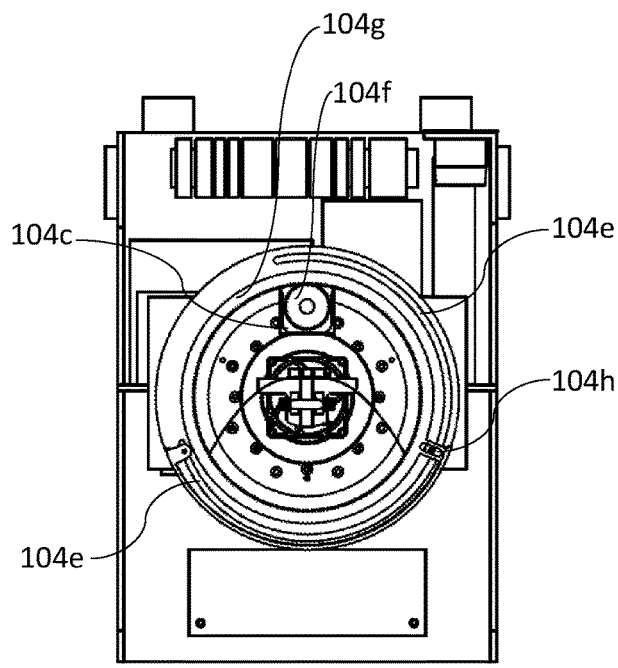
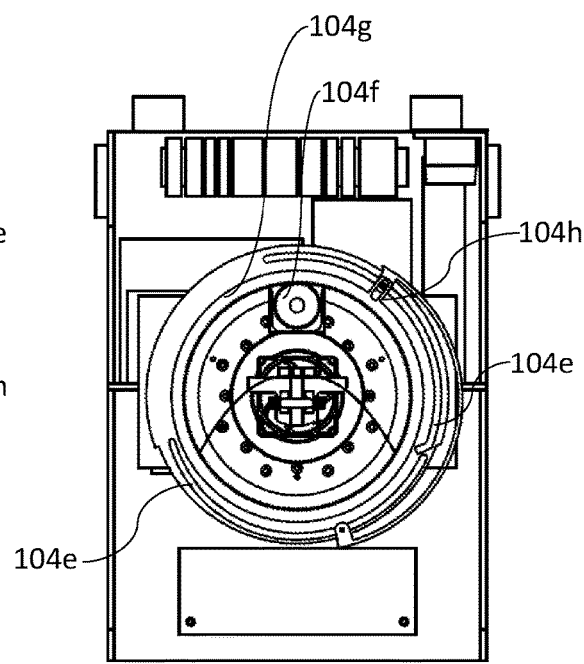
Fig. 12a
Fig. 12b
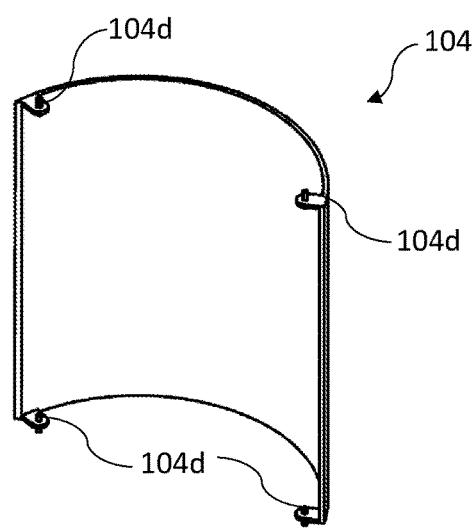
Fig. 12c

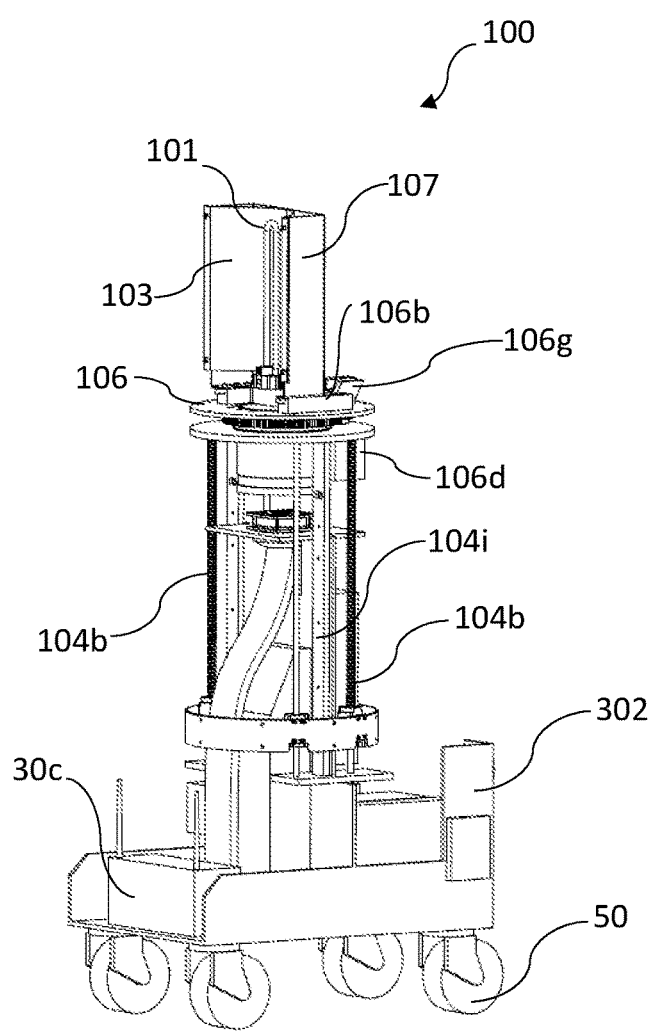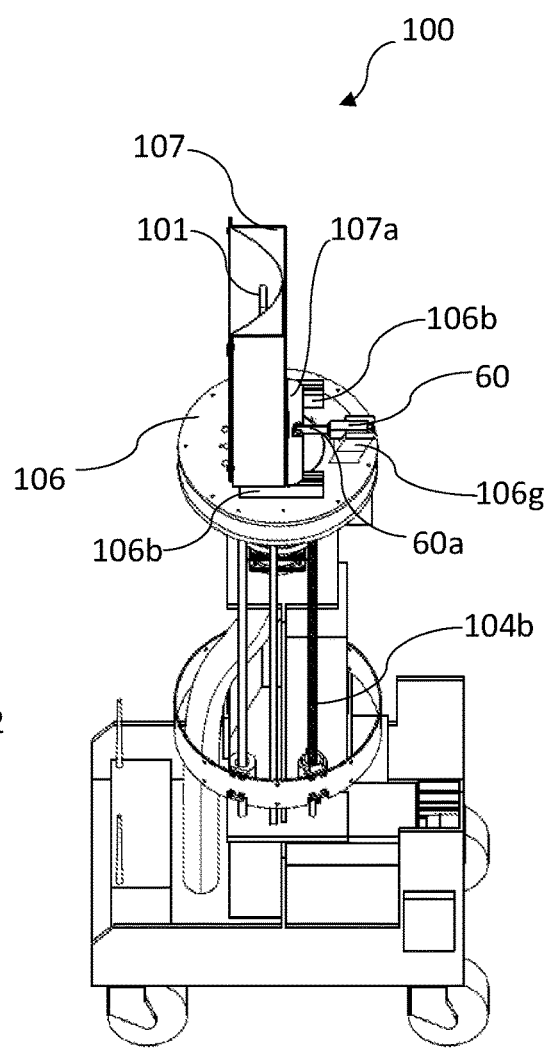
Fig. 13
Fig. 14

PULSED XENON ULTRAVIOLET (UV) DISINFECTION SYSTEM

FIELD OF DISCLOSURE

The present disclosure relates generally to field of ultraviolet (UV) based disinfection systems. Particularly, but not exclusively, the present disclosure relates to a pulsed UV disinfection system for treating objects present inside a closed space or an area surrounding the disinfection system.

TECHNICAL BACKGROUND

The information in this section merely provides background information related to the present disclosure and may not constitute prior art(s).

It is well known in the art to use ultraviolet (UV) light/radiation for disinfection of the one or more surfaces and/or objects to kill microorganisms residing upon the surfaces and/or objects. Examples of such applications include but are not limited to sterilization of tools, fluid and object disinfection, and room/area decontamination. The ultraviolet light, preferably the dose of ultraviolet electromagnetic radiation subtype C (UVC) light alters the genetic (DNA) material in cells so that bacteria, viruses, and other microorganisms can no longer reproduce. Ultraviolet light is classified into three categories: UV-C, from about 200 nanometers (nm) to about 280 nm; UV-B, from about 280 nm to about 315 nm; and UV-A, from about 315 nm to about 400 nm. Generally, UV-C light is considered as "germicidal", i.e. it deactivates the DNA of bacteria, viruses and other pathogens and thus destroys their ability to multiply and cause any sort of diseases to humans. Thus, UV-C light effectively results in sterilization of the microorganisms.

The existing UV disinfectant systems comprise a light source as a major component which does the disinfection of nearby objects. The light source may be a mercury bulb, a pulsed xenon UV bulb or an UV LED. The mercury bulb is configured to output almost a single wavelength light i.e. UV-C light. Xenon pulsed UV bulb has xenon gas as the primary source and is configured to output continuous spectrum of light which extends from UV region to IR region of spectrum. Further, the UV LED is adapted to output only single wavelength of light. The existing UV disinfectant systems are increasingly used in area/room disinfection applications as pulsed UV light has been shown to significantly reduce the number of pathogenic microorganisms in an area/room in a short period of time. In addition, pulsed UV light has shown to reduce the number of pathogenic microorganisms within a room/area to a level considered much less harmful to human health. The manufacturers are focusing on developing UV disinfection systems adapted to treat not only the objects placed inside a room but also the atmosphere/air inside a room/area.

Further, the existing UV disinfection system comprises a lamp, optical filter, ozone filter, reflector, support assembly and other components to facilitate the functioning of the system. Such components are adapted to perform various functions such as reflecting UV light coming out from the lamp into the atmosphere, providing safety to human beings after treating the space and/or objects in the room. The existing systems do not facilitate effective dispersion of UV light and are not flexible enough to control the dispersion of the UV light for different sanitization requirements. The manufacturers have sought, proposed, and implemented different solutions to improve the functionality of UV disinfection systems. One such solution include providing a rotatable head assembly in the UV disinfection system. The rotatable head assembly comprises a lamp and a reflector. Further, the head assembly is adapted to rotate about vertical axis with the help of actuators.

However, the head assembly of existing UV disinfection system is adapted to rotate only at preferred angle. A continuous 360° rotation of the head assembly is not possible as the head assembly must traverse through the same path as it travelled before. Further, when the head assembly starts to rotate from 0°, the multiple 360° rotations of head assembly is not possible without changing the direction of rotation because of the mechanical constraints imposed by plurality of power cables going into the lamp. As these cables are required to supply power to the lamp to facilitate emission of UV light. Further, the multiple 360° rotations of the head assembly may result in twisting of plurality of cables and eventually breaking the cables causing a safety hazard. Further, the UV disinfection system is required to move in different orientations after each treatment cycle to facilitate treatment of remaining objects placed at different locations.

In view of above, there is an immense need in the art to provide a solution to overcome the drawbacks/problems/disadvantages associated with existing UV disinfection systems.

SUMMARY OF THE DISCLOSURE

The present disclosure discloses an improved pulsed UV disinfection system providing better and effective treatment of objects located at different locations inside a room. In an embodiment, the present disclosure therefore provides a UV disinfection system utilizing at least one lamp as a light source for emitting UV rays. The UV rays emitted by the lamp may be projected on different objects facilitate treatment of the objects present inside a room and surrounding the system. Additional features and advantages are realized through the technicalities of the present disclosure. Other embodiments and aspects of the disclosure are described in detail herein and are a part of the claimed disclosure.

The present disclosure relates to a ultraviolet (UV) disinfection system. The system comprises a head portion mounted on an intermediate portion of the UV disinfection system. The head portion comprises at least one UV lamp and a shutter mechanism. The shutter mechanism comprises a shutter adapted to isolate the UV lamp from surroundings. The shutter is defined with at least two elongated holes configured to receive at least one ball screw and at least one linear guide rail. The at least one ball screw is coupled with a first output shaft of a first motor to facilitate reciprocating movement of the shutter. The reciprocating movement of the shutter enables opening and closing of the shutter during operating and non-operating conditions respectively.

In an embodiment, the UV disinfection system comprises at least one reflector positioned around the at least one UV lamp. The at least one reflector is configured to direct UV rays emitted from the UV lamp to the surroundings.

In an embodiment, a carriage is engaged with the at least one ball screw and the at least one linear guide rail. The carriage comprises a plurality of inner threads adapted to engage with a plurality of outer threads formed on the ball screw to facilitate linear movement of the carriage along a length of the ball screw.

In an embodiment, the carriage is removably connected to the shutter, such that the linear movement of the carriage is transmitted to the shutter to facilitate reciprocating movement of the shutter.

In an embodiment, the first motor is communicatively connected to a fourth controller to govern operation of the shutter mechanism.

In an embodiment, the intermediate portion comprising a third plate configured to provides provisions for rotatably connecting the at least one ball screw and the at least one linear guide rail to the third plate.

In another embodiment, the shutter comprises at least two cams adapted to be received in a circumferential slot formed on the head portion. The slot and the cam arrangement facilitates manual opening and/or closing of the shutter in circumferential direction.

In another embodiment of the present disclosure, a UV disinfection system comprises a head portion mounted on an intermediate portion of the UV disinfection system. The head portion comprises at least one UV lamp and at least one reflector. The at least one reflector is configured to direct UV rays emitted from the at least one UV lamp. The reflector is connected to a frame and the frame is connected to a first drive shaft of a first actuator. The first actuator facilitates linear movement of the at least one reflector connected to the frame to vary reflection pattern of the UV rays.

In an embodiment, the frame comprises a first flange and a pair of second flanges. The first flange extends from a rear wall of the frame to connect the first drive shaft with the frame, and each flange of the pair of second flanges comprises a plurality of guiding knobs.

In an embodiment, the head portion comprises a base plate having a hole, and a plurality of teeth formed along a circumference of the base plate.

In an embodiment, the hole is provided on the base plate to receive a socket for connecting the at least one UV lamp.

In an embodiment, at least two blocks are mounted on an upper surface of the base plate, and each of the at least two blocks are provided with a slot adapted to receive the plurality of guiding knobs, to facilitate linear movement of the reflector fixed with the frame.

In another embodiment of the present disclosure, a UV disinfection system comprises a head portion mounted on an intermediate portion of the UV disinfection system. The head portion comprises at least one UV lamp and a reflector configured to direct UV rays emitted from the at least one UV lamp. The reflector is connected to a shape changing mechanism. The mechanism comprises a pair of internal arms pivotably connected to the reflector through a first bracket, and a pair of external arms pivotably connected to the reflector through a second bracket. The first bracket and the second bracket are connected to each other by a second actuator, and the second bracket is connected to the second actuator through a second drive shaft to facilitate changing of shape of the reflector.

In an embodiment, the first bracket is defined with a wedge-shaped flange provided at center of the first bracket to provide support to the reflector.

In an embodiment, the reflector is manufactured from a flexible material configured to reflect the UV rays emitted by the at least one UV lamp.

In an embodiment, the second actuator is configured to govern linear movement of the second drive shaft to facilitate pivotal movement of the external arms in order to change shape of the reflector.

In an embodiment, the at least one UV lamp is a pulsed xenon UV lamp.

In an embodiment, the first actuator and the second actuator are defined as linear actuators.

In an embodiment, the system comprises a lower portion configured to mount a plurality of wheels to facilitate mobility of the UV disinfection system.

In an embodiment, the plurality of teeth on the base plate are configured to engage with a plurality of teeth formed on a second output shaft of a second motor to facilitate oscillation of the reflector connected to the base plate.

The above summary is illustrative only and is not intended to be in any way limiting. In addition to the illustrative aspects and features described above, further aspects and features will become apparent by reference to the drawings and the following detailed description.

BRIEF DESCRIPTION OF THE ACCOMPANYING FIGURES

Further aspects and advantages of the present invention will be readily understood from the following detailed description with reference to the accompanying figure(s). The figure(s) together with a detailed description below, are incorporated in and form part of the specification, and serve to further illustrate the embodiments and explain various principles and advantages, in accordance with the present invention wherein:

FIG. 1: illustrates a front view of an UV disinfection system, in accordance with an embodiment of the present disclosure;

FIG. 2: illustrates a side view of the UV disinfection system of FIG. 1;

FIG. 4 illustrates a front perspective view of the UV disinfection system of FIG. 1, without intermediate and lower casing;

FIG. 5 illustrates a rear perspective view of the UV disinfection system of FIG. 1, without intermediate and lower casing;

FIG. 7, FIG. 8 illustrate a front perspective view of the UV disinfection system of FIG. 4, with retractable shutter mechanism depicting open and closed position of the shutter;

FIG. 12a illustrates top view of the UV disinfection system of FIG. 11a;

FIG. 12b illustrates top view of the UV disinfection system of FIG. 11b;

FIG. 12c illustrates perspective view of a shutter panel assembled to the UV disinfection system of FIG. 11a;

FIG. 13 illustrates front perspective view of another embodiment of the UV disinfection system, in accordance with an embodiment of the present disclosure;

FIG. 14 illustrates side perspective view of the UV disinfections system of FIG. 13 of the present disclosure;

Figures 15A, 15B, 15C:
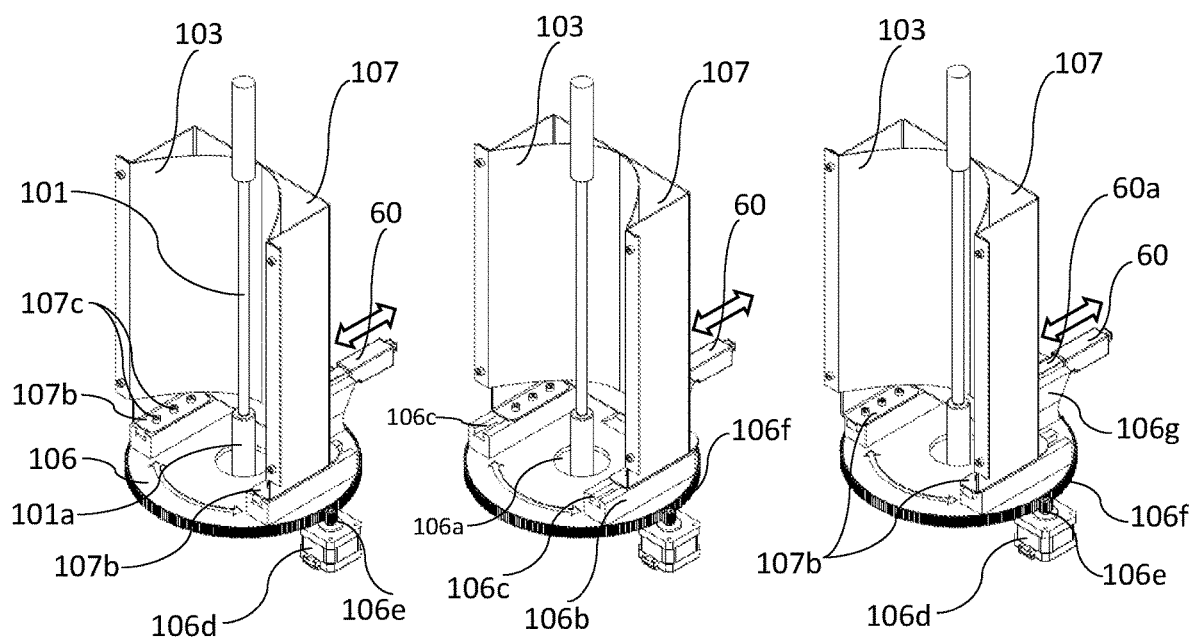
Figure 16:
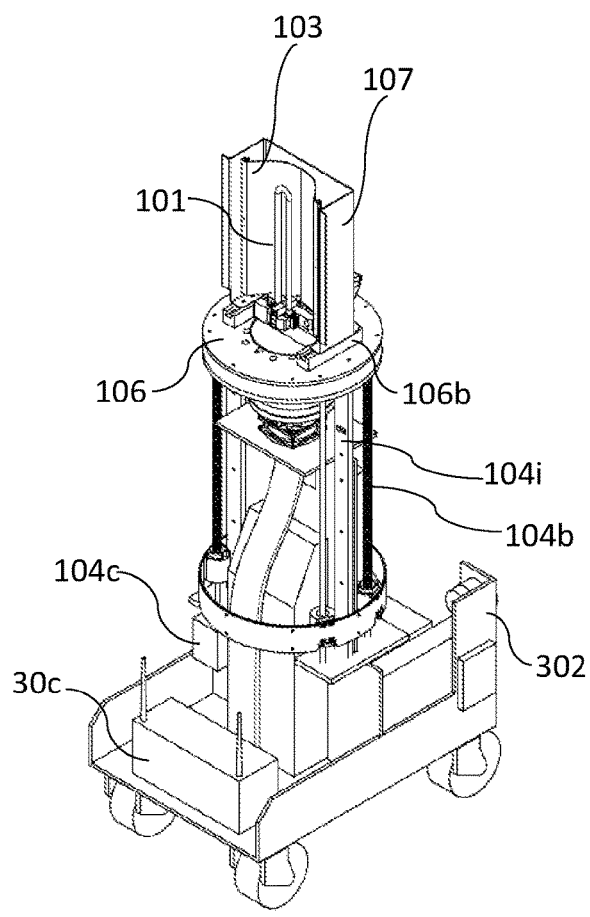
Figure 17:
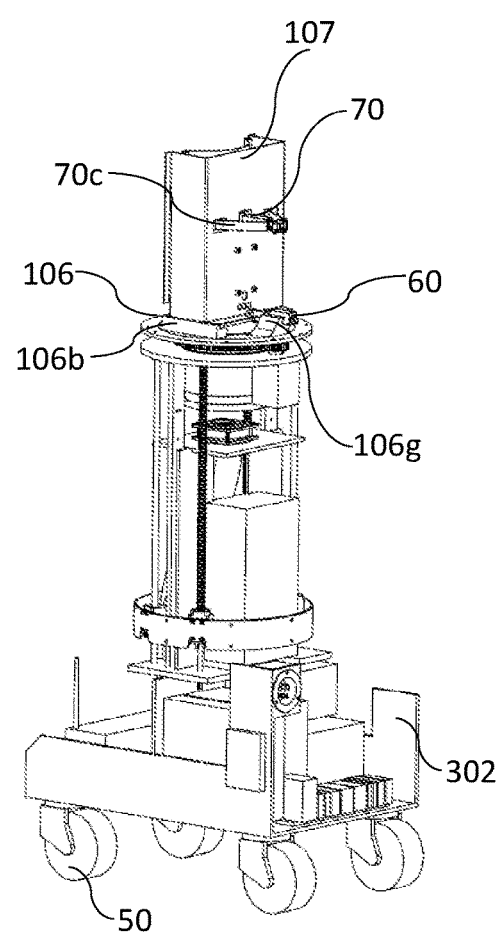
Figure 18:
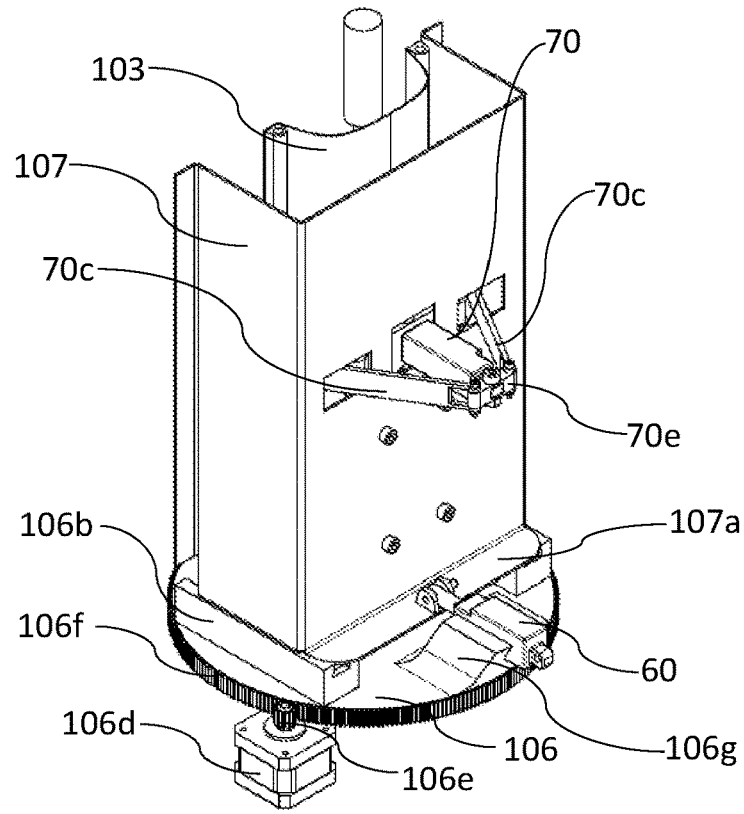
Figure 19:
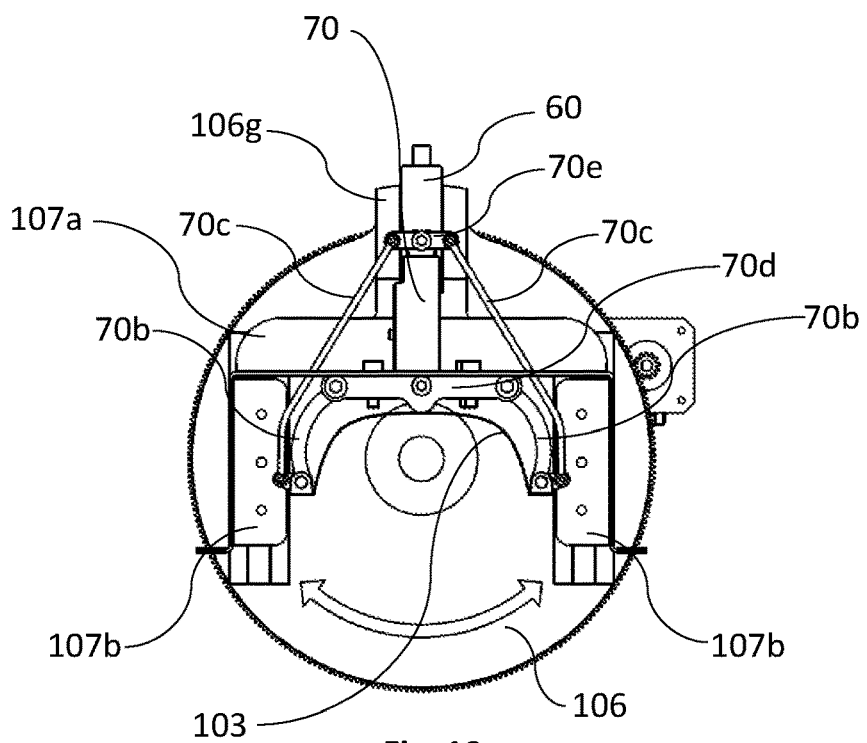
Figures 20A, 20B:
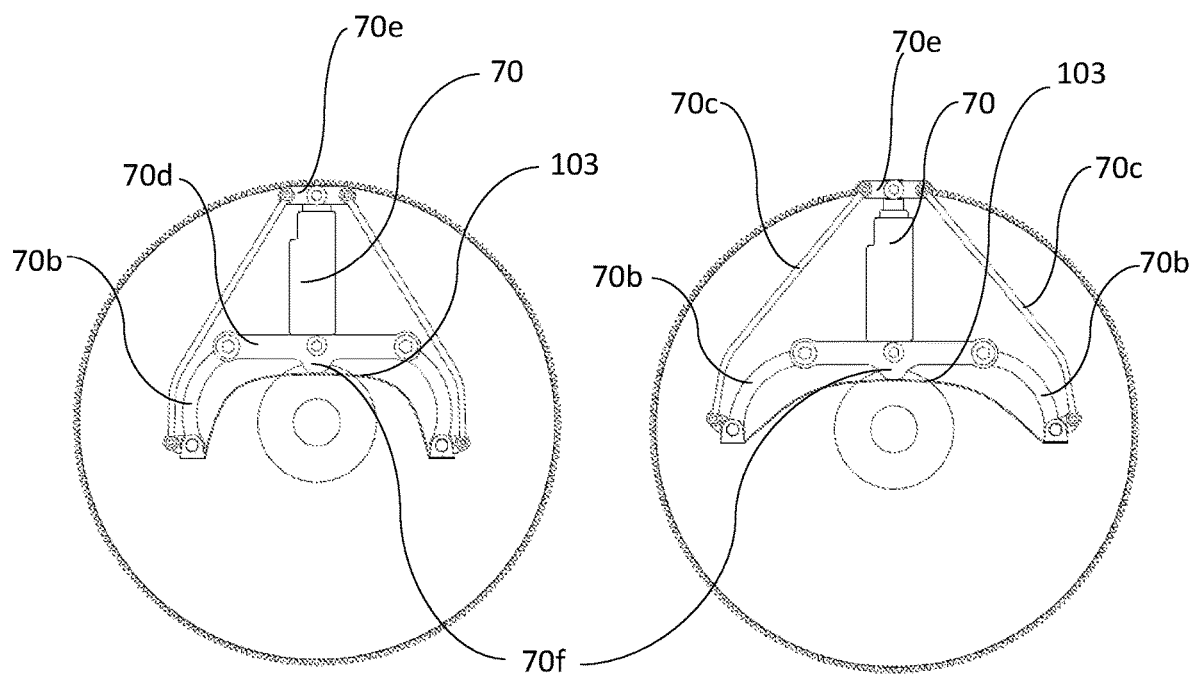
Figure 20C:
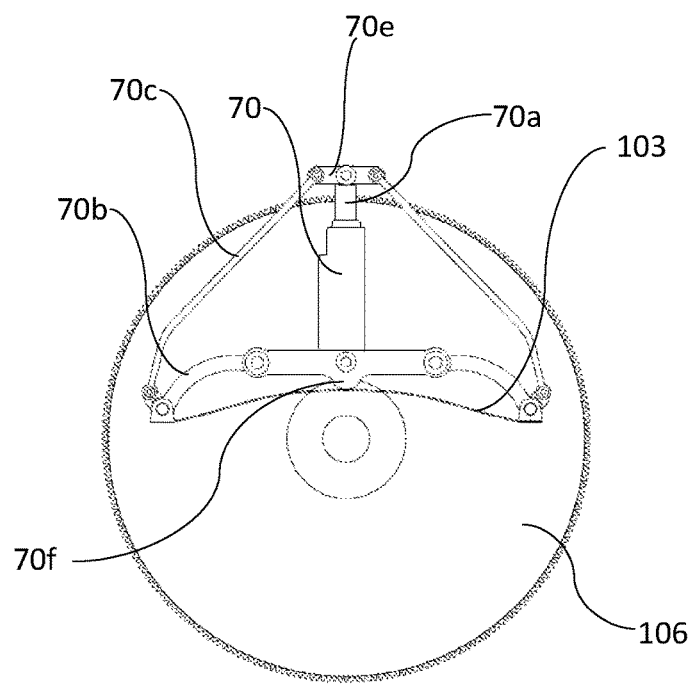

FIG. 15(a)-15(c) illustrate linear movement of reflector of the UV disinfection system of FIG. 13;

FIG. 16 illustrates front perspective view of another embodiment of the UV disinfection system, in accordance with an embodiment of the present disclosure;

FIG. 17 illustrates rear perspective view of the UV disinfection system of FIG. 16;

FIG. 18 illustrates a rear perspective view of a mechanism for changing shape of the reflector of the UV disinfection system of FIG. 16;

FIG. 19 illustrates a top view of the mechanism for changing shape of the reflector of the UV disinfection system of FIG. 18;

FIG. 20(a)-20(c) illustrate different shapes of the reflector of the UV disinfection system in accordance with an embodiment of the present disclosure.

Skilled artisans will appreciate that elements in the drawings are illustrated for simplicity and have not necessarily been drawn to scale. For example, the dimensions of some of the elements in the drawings may be exaggerated relative to other elements to help to improve understanding of embodiments of the present invention.

DETAILED DESCRIPTION OF THE ACCOMPANYING FIGURES

While the invention is susceptible to various modifications and alternative forms, specific embodiment thereof has been shown by way of example in the figures and will be described in detail below. It should be understood, however that it is not intended to limit the invention to the particular forms disclosed, but on the contrary, the invention is to cover all modifications, equivalents, and alternative falling within the spirit and the scope of the invention.

Before describing in detail embodiments, it is to be noted that a person skilled in the art can be motivated from the present disclosure and modify the various constructions of assembly, which are varying from system to system. However, such modification should be construed within the scope and spirit of the invention. Accordingly, the drawing(s) are showing only those specific details that are pertinent to understanding the embodiments of the present invention so as not to obscure the disclosure with details that will be readily apparent to those of ordinary skill in the art having benefit of the description herein.

The terms "comprises", "comprising", or any other variations thereof, are intended to cover a non-exclusive inclusion, such that a setup, device that comprises a list of components does not include only those components but may include other components not expressly listed or inherent to such setup or device. In other words, one or more elements in a system or apparatus proceeded by "comprises . . . a" does not, without more constraints, preclude the existence of other elements or additional elements in the system or apparatus.

Accordingly, the present disclosure relates to a UV disinfection system. The UV disinfection system is a mobile system that can be used in various applications to disinfect objects with the help of UV rays. The system can be used in hospitals to disinfect an area/room and the objects present in the room. Examples of applications include but are not limited to sterilization of tools, object disinfection, and closed room/area decontamination. The UV disinfection system utilizes at least one UV lamp as a light source for emitting pulsed UV rays. The UV rays are considered as a germicidal rays which damages/alters genetic material in cells so that bacteria, viruses, and other microorganisms can no longer reproduce. The microorganisms may be considered dead and the risk of disease from them is eliminated.

The at least one UV lamp may comprise xenon gas doped with other gases to increase the UVC output. For example—the UV lamp may be filled with the xenon gas doped with the krypton gas to regulate spectral output from the UV lamp. The doping or mixing of gases in a predetermined ratio may change the chemical behavior of the UV lamp and therefore, the UV spectrum may get varied to achieve better efficiency and UV output from the UV lamp.

In an exemplary embodiment, the UV lamp is preferably a xenon lamp utilizing xenon gas as the primary filler and adapted to emit exceptionally smooth continuous spectrum of light which extends from deep UV region to IR region of spectrum. The high electric discharge onto the xenon gas present in the lamp results in generation and emission of rays in the form of UV rays and IR rays. The xenon lamp in accordance with the present disclosure is adapted to emit continuous pulse of UV rays to effectively perform the treatment of the objects present inside the room.

In another exemplary embodiment, the UV lamp may be filled with a combination of different gases in a predetermined ratio to facilitate increase in emission of UV rays in operating condition of the UV disinfection system. The emission of UV rays may take place as soon as a specified amount of charge or electric current is allowed to pass through the mixture of gases present in the UV lamp of the system. The charge may heat the gases present in the UV lamp, thereby resulting in emission of UV rays by varying the UV spectrum to achieve better efficiency and UV output from the UV lamp.

The UV disinfection system comprises a head portion, an intermediate portion and a lower portion. The head portion comprises a lamp as a light source enclosed in a housing. The lamp is adapted to emit the UV rays of preferred wavelength. The lamp is preferably a xenon lamp adapted to emit exceptionally smooth continuous spectrum of light rays which extends from deep UV region to IR region of spectrum. However, the lamp may be any UV light source adapted to emit light rays within the UV region of the spectrum. The UV rays emitted by the lamp is adapted to deactivate, destroy, or prevent the growth of disease-carrying microorganisms in the area. The lamp is removably disposed in the housing and can be replaced after a particular period of time of usage or removed during maintenance of the housing. The lower portion of the disinfection system may be supported on plurality of support wheels to facilitate mobility of the system. The lower portion of the system may comprise a robotic platform having specific electronic components and motorized wheels to facilitate autonomous movement of the system. Each of the wheels mounted on the lower portion may be powered by dedicated motors or by a single motor coupled to the wheels by a power transmission unit. The lower portion comprises plurality of electronic components to facilitate flashing of lamp and to control operation of various actuators connected to different components of the system.

The head portion may have but not limited to have a parabolic, elliptical, cylindrical shape or any other desired shape as per the requirement. The reflector is positioned around the lamp in the head portion of the UV disinfection system. The reflector is removably connected to a base plate having a central cutout and a plurality of teeth formed on outer circumference of the base plate. The central cutout is configured to receive a socket to which the lamp is communicatively coupled. The socket may be defined having a hollow conduit adapted to receive a plurality of wires to supply power to the lamp. The central cutout provided on the base plate also prevents twisting of the plurality of wires during continuous rotation of the lamp in an operating condition. The operating condition is defined as a state/condition in which the UV disinfection system is utilized for sterilization of tools, objects disinfection, and room/area decontamination by using the pulsed UV rays emitted by the lamp. Further, the non-operating condition is defined as a state/condition in which the UV disinfection system is kept idle.

In an embodiment, an ultraviolet (UV) disinfection system comprises a head portion mounted on an intermediate portion of the UV disinfection system. The head portion comprises at least one UV lamp and a shutter mechanism. The shutter mechanism comprises a shutter adapted to isolate the UV lamp from surroundings. The shutter is defined with at least two elongated holes configured to receive at least one ball screw and at least one linear guide rail. The at least one ball screw is coupled with a first output shaft of a first motor to facilitate reciprocating movement of the shutter. The reciprocating movement of the shutter enables opening and closing of the shutter during operating and non-operating conditions respectively.

In an embodiment, the UV disinfection system comprises at least one reflector positioned around the at least one UV lamp. The at least one reflector is configured to direct UV rays emitted from the UV lamp to the surroundings.

In an embodiment, a carriage is engaged with the at least one ball screw and the at least one linear guide rail. The carriage comprises a plurality of inner threads adapted to engage with a plurality of outer threads formed on the ball screw to facilitate linear movement of the carriage along a length of the ball screw.

In an embodiment, the carriage is removably connected to the shutter, such that the linear movement of the carriage is transmitted to the shutter to facilitate reciprocating movement of the shutter.

In an embodiment, the first motor is communicatively connected to a fourth controller to govern operation of the shutter mechanism.

In an embodiment, the intermediate portion comprises a third plate which provides provisions for rotatably connecting the at least one ball screw and the at least one linear guide rail to the third plate.

In another embodiment, the shutter comprises at least two cams adapted to be received in a circumferential slot formed on the head portion. The slot and the cam arrangement facilitates manual opening and/or closing of the shutter in circumferential direction.

In another embodiment of the present disclosure, a UV disinfection system comprises a head portion mounted on an intermediate portion of the UV disinfection system. The head portion comprises at least one UV lamp and at least one reflector. The at least one reflector is configured to direct UV rays emitted from the at least one UV lamp. The reflector is connected to a frame and the frame is connected to a first drive shaft of a first actuator. The first actuator facilitates linear movement of the at least one reflector connected to the frame to vary reflection pattern of the UV rays.

In an embodiment, the frame comprises a first flange and a pair of second flanges. The first flange extends from a rear wall of the frame to connect the first drive shaft with the frame, and each flange of the pair of second flanges comprises a plurality of guiding knobs.

In an embodiment, the head portion comprises a base plate having a hole, and a plurality of teeth formed along a circumference of the base plate.

In an embodiment, the hole is provided on the base plate to receive a socket for connecting the at least one UV lamp.

In an embodiment, at least two blocks are mounted on an upper surface of the base plate, and each of the at least two blocks are provided with a slot adapted to receive the plurality of guiding knobs, to facilitate linear movement of the reflector fixed with the frame.

In another embodiment of the present disclosure, a UV disinfection system comprises a head portion mounted on an intermediate portion of the UV disinfection system. The head portion comprises at least one UV lamp and a reflector configured to direct UV rays emitted from the at least one UV lamp. The reflector is connected to a shape changing mechanism. The mechanism comprises a pair of internal arms pivotably connected to the reflector through a first bracket, and a pair of external arms pivotably connected to the reflector through a second bracket. The first bracket and the second bracket are connected to each other by a second actuator, and the second bracket is connected to the second actuator through a second drive shaft to facilitate changing of shape of the reflector.

In an embodiment, the first bracket is defined with a wedge-shaped flange provided at center of the first bracket to provide support to the reflector.

In an embodiment, the reflector is manufactured from a flexible material configured to reflect the UV rays emitted by the at least one UV lamp.

In an embodiment, the second actuator is configured to govern linear movement of the second drive shaft to facilitate pivotal movement of the external arms in order to change shape of the reflector.

In an embodiment, the at least one UV lamp is a pulsed xenon UV lamp.

In an embodiment, the first actuator and the second actuator are defined as linear actuators.

In an embodiment, the system comprises a lower portion configured to mount a plurality of wheels to facilitate mobility of the UV disinfection system.

In an embodiment, the plurality of teeth on the base plate are configured to engage with a plurality of teeth formed on a second output shaft of a second motor to facilitate oscillation of the reflector connected to the base plate.

Reference will now be made to the exemplary embodiments of the disclosure, as illustrated in the accompanying drawings. Wherever possible same numerals will be used to refer to the same or like parts.

Embodiments of the disclosure are described in the following paragraphs with reference to FIGS. 1 to 20.

Figure 1:
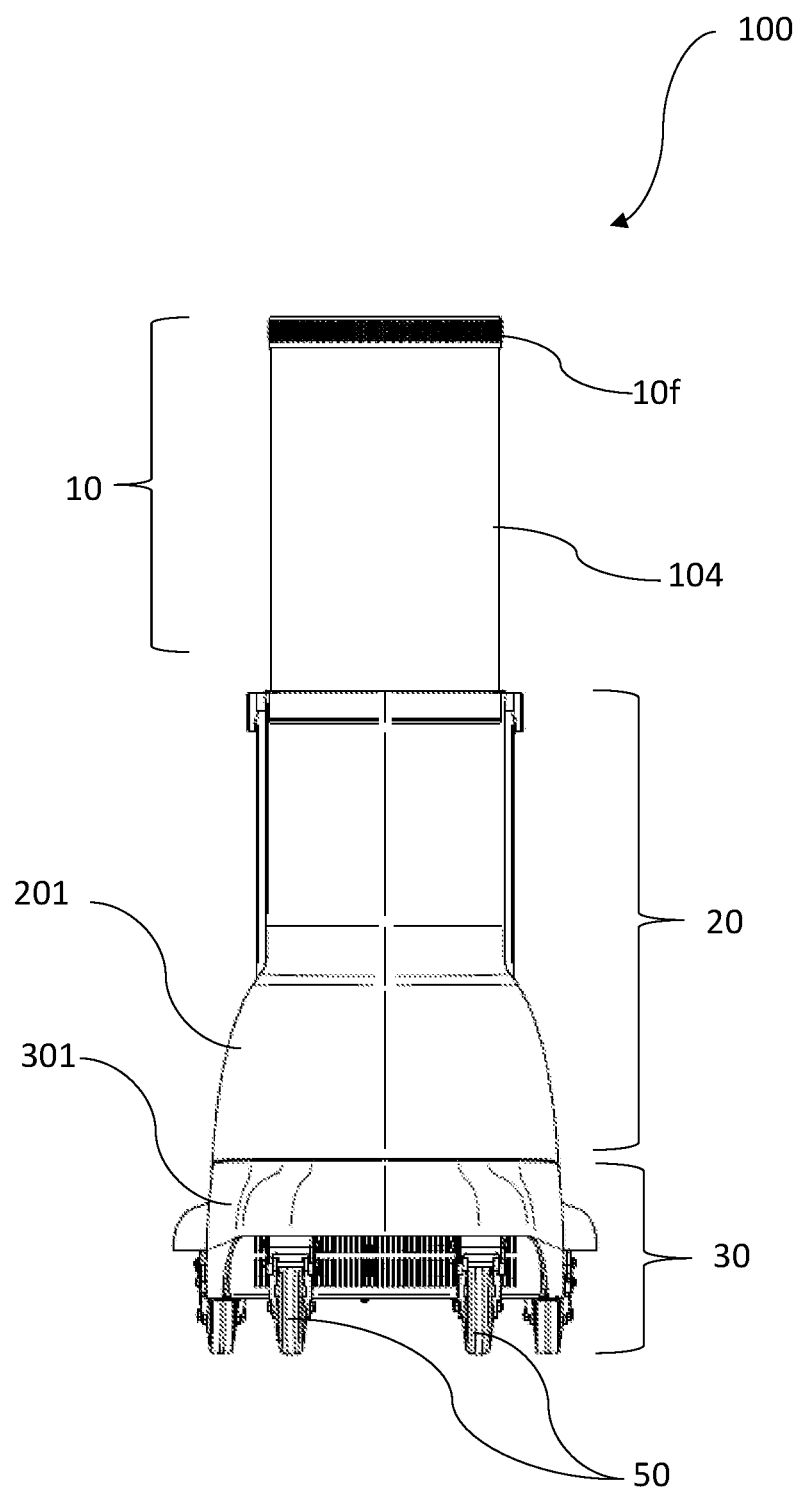
Figures 2, 3:
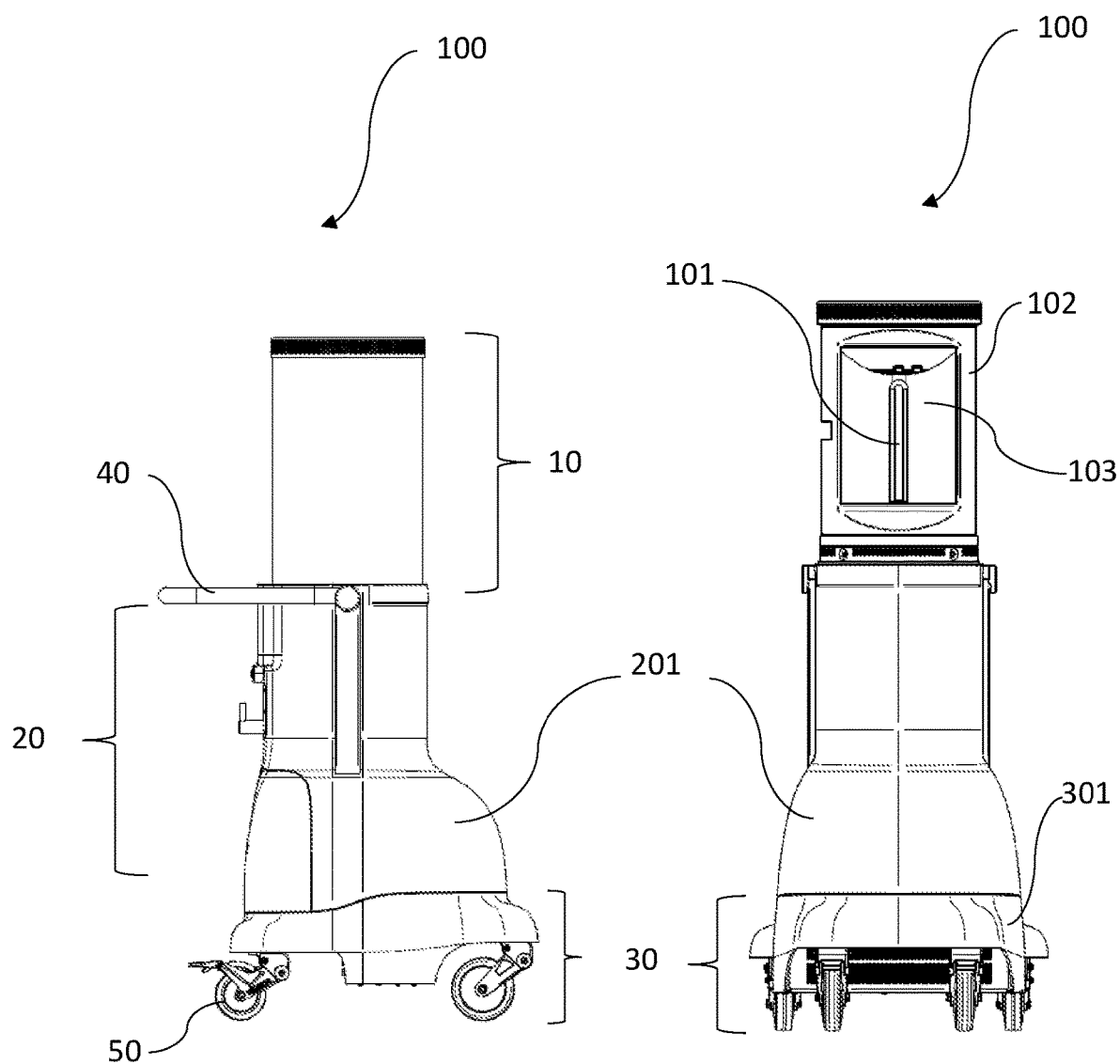
FIG. 3 illustrates a front view of the UV disinfection system of FIG. 1 with shutter in an open configuration.

As shown in FIGS. 1-3, a UV disinfection system 100 (hereinafter referred to as "system") comprises a head portion 10, an intermediate portion 20 and a lower portion 30. The head portion 10 comprises a lamp 101, a housing 102 for the lamp 101 and a reflector 103 to direct or reflect UV rays in a preferred direction. The head portion 10 is mounted on the intermediate portion 20 by means of fasteners but not limited to the same. The head portion 10 may removably be attached to the intermediate portion 20 by mechanical locking means for example—snap-fit locking means, inter-locking of elements of the head portion 10 and the intermediate portion 20, etc. The head portion 10 may be adapted to extend or retract to vary height of the system 100 as per the requirement and to provide better reach of the UV rays for target areas at different heights and locations. The head portion 10 may be attached to a plurality of vertically arranged linear guides to provide a desired path for vertical movement of the head portion 10. The extending and retracting of the head portion 10 may also be achieved by an actuator placed inside the intermediate portion 20. The actuator may comprise electrical, hydraulic, pneumatic, or mechanical means to extend and/or retract the head portion 10 with respect to the intermediate portion 20 of the system 100. Further, even a manual actuator/force can be utilized for manually retracting and extending the head portion 10 with the help of counterbalancing springs, bellows, etc.

The lamp 101 in accordance with the present disclosure is preferably a xenon lamp. The lamp 101 is configured to emit the UV rays to facilitate treatment of the objects present inside the room and/or surrounding the system 100. The lamp 101 may be oriented in a horizontal plane or in a vertical plane. The lamp 101 is removably disposed to the head portion 10 in order to facilitate lamp replacement after a particular period of time. The lamp 101 in accordance with the present disclosure is stationary i.e. not moveable with respect to the head portion 10 of the UV disinfection system 100. The fixed position of lamp 101 in the head portion 10 facilitates uniform and continuous emission of the UV rays onto exterior of the system 100.

Figure 6:
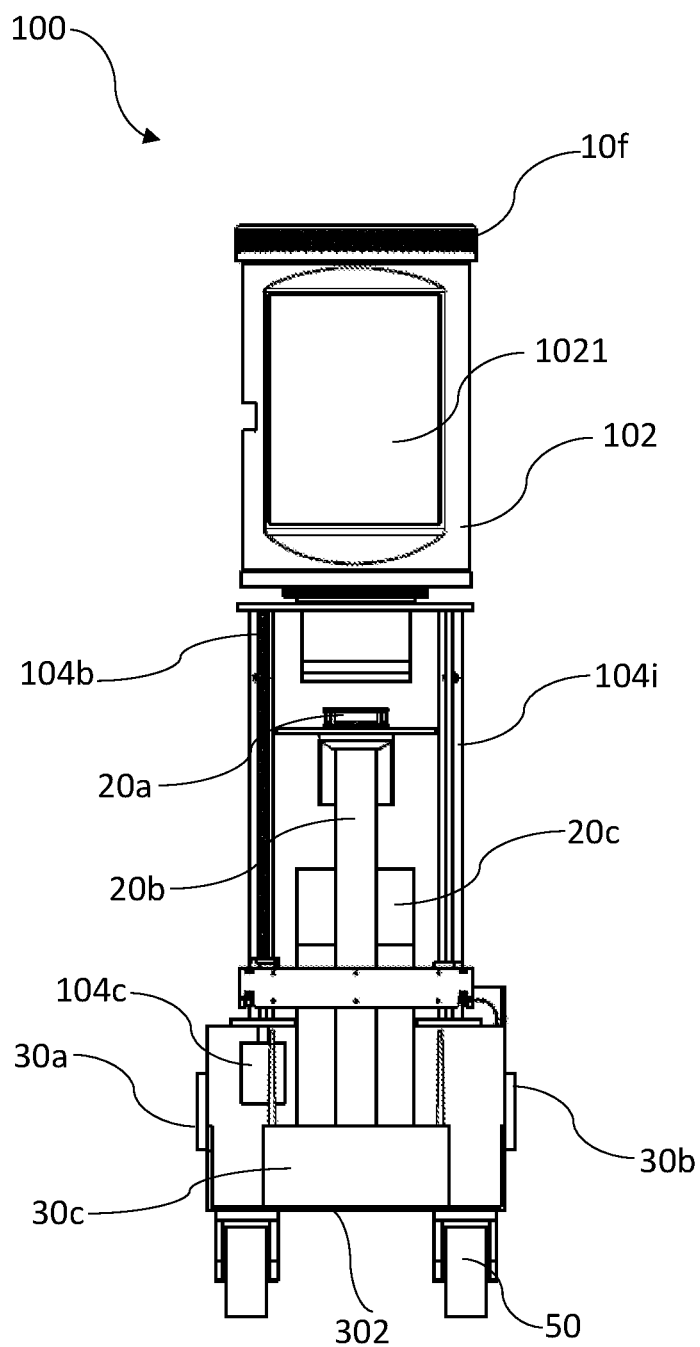
FIG. 6 illustrates a front view of the UV disinfection system of FIG. 1, without intermediate and lower casing.

The housing 102 enclosing the lamp 101 can be made up of any suitable material such as quartz which is transparent to the UV light emitted by the lamp 101. The connecting means for removably securing the head portion 10 to the intermediate portion 20 is provided at bottom surface of the housing 102. Referring to FIG. 6, the housing 102 may be defined with a window 1021 made from a quartz material to provide specific region for allowing dispersion of the UV rays emitted by the lamp 101. The housing 102 acts as a protecting element for plurality of components mounted in the head portion 10 of the system 100. For instance, the housing 102 protects the lamp 101, the reflector 103 and different mechanisms associated with the reflector 103 from foreign particles i.e. dust, moisture, etc. The head portion 10 comprises a shutter mechanism to facilitate covering of the housing 102, when the system 100 is in "non-operating" condition. The "non-operating" condition may be defined as a condition/state of the system 100 at which the system 100 is not configured to perform disinfection of the objects, tools, areas etc surrounding the system 100. The shutter mechanism comprises a shutter 104 adapted to isolate the lamp 101 from surroundings in non-operating conditions. The "operating" condition mat be defined as a condition/state of the system 100 at which the system 100 is utilized to perform disinfection of the objects, tools, areas etc surrounding the system 100.

In an exemplary embodiment, the head portion 10 is fastened to the intermediate portion 20 by means of bolts and nuts or screws or likewise. Referring to FIG. 2, a handle 40 is assembled at a junction of the head portion 10 and the intermediate portion 20 to facilitate transportation of the system 100. The handle 40 is preferably made from a polymeric material having high tensile strength. However, the material for manufacturing the handle 40 may be varied and may depend on the size and configuration of the system 100. The intermediate portion 20 and the lower portion 30 are covered by an intermediate casing 201 and a lower casing 301. The intermediate casing 201 and the lower casing 301 provide aesthetic appeal to the system 100 by covering all the electronic, electrical elements and mechanical components of the system 100. The intermediate casing 201 and the lower casing 301 also prevent the electrical components from malfunctioning due to entering of the foreign particles for example—dust, moisture etc.

FIGS. 4-6, depicting different views of the system 100 are now being referred to explain interconnections and working of different electrical and electronic components mounted on the head portion 10, the intermediate portion 20 and the lower portion 30 of the system 100.

In an exemplary embodiment, the head portion 10 comprising a first plate 105 and a base plate 106. The first plate 105 is provided with provisions to mount an exhaust fan 10a. The first plate 105 is disposed at a top end of the head portion 10. The exhaust fan 10a is configured to allow flow of treated air from the system 100 into the surrounding. Below the exhaust fan 10a, a filter 10b is removably mounted, as shown in FIG. 5. The filter 10b is preferably a carbon filter but not limited to the same. The filter 10b may also be a removable charcoal filter to neutralize ozone elements present in the air passing through the lamp 101 before ejection of the treated air into the surrounding through the exhaust fan 10a. The exhaust fan 10a is surrounded by an exhaust air grill 10f mounted on the first plate 105 of the head portion 10, as shown in FIG. 6.

A first mesh plate 10c is fixed to the filter 10b and said first mesh plate 10c is positioned below the filter 10b. The first mesh plate 10c is configured to provide support to the filter 10b while maintaining the air flow. The exhaust fan 10a is mounted on an upper surface of the first plate 105 and the filter 10b & the first mesh plate 10c are mounted on a lower surface of the first plate 105 of the head portion 10. A second mesh plate 10d may be provided at bottom of the lamp 101 and said second mesh plate 10d may be mounted on the base plate 106 to filter air ejected by an intake fan 20a. The head portion 10 further comprises a frame 107 fastened to the reflector 103. The frame 107 may be fitted with a first controller 10e, according to an exemplary embodiment of the present disclosure. The first controller 10e may defined as a high voltage trigger controller, configured to trigger the lamp 101 during high voltage condition.

The intermediate portion 20 comprises a second plate 202 and a third plate 203, as shown in FIG. 5. The second plate 202 is provided with provisions to mount the head portion 10 onto the intermediate portion 20. The second plate 202 is positioned below the base 106 of the head portion 10. The second plate 202 provides stability to the head portion 10 by connecting the head portion 10 to the intermediate portion 20. The intake fan 20a is fluidly connected to a conduit 20b for facilitating intake of the ambient air from the surrounding, as shown in FIG. 4 and FIG. 6. The intermediate portion 20 is provided with provisions to mount a second controller 20c and a third controller 20d. The second controller 20c is preferably a high voltage controller to prevent supply of power to different electronic components during abrupt increase in voltage. The second controller 20c contain PFN i.e. Pulse Forming Network electric circuit, which accumulates electric energy over a comparatively long time and then releases stored energy in the form of a relatively square pulse of comparatively brief duration for various pulsed power applications. The second controller 20c may contain energy storage components such as capacitors, inductors and likewise which are charged by means of high voltage power source and then rapidly discharged into the lamp 101. The third controller 20d is preferably a UV lamp controller configured to govern operation of the UV lamp 101 based on the input provided by a user. The third controller 20d is configured to regulate the supply of current to facilitate variation in amount of the UV rays emitted by the lamp 101, depending on the application of the system 100.

During operating condition of the system 100, the intake fan 20a is configured to allow the flow cold air from the surrounding into the lamp housing 102 through the conduit 20b. The intake fan 20a comprising an outlet surface is fitted with the second mesh plate 10d. The cold air ejected by the intake fan 20a is allowed to pass through the second mesh plate 10d before entering the housing 102. The second mesh plate 10d provides a protective plate or element in between the lamp 101 and the intake fan 20a. The second mesh plate 10d prevents intrusion of fasteners (for example—nuts, bolts, screws and likewise) into the intake fan 20a during servicing or maintenance of the system 100. The cold air is then allowed to pass through the first mesh plate 10c into the filter 10b. The exhaust fan 10a placed on top of the filter 10b is configured to create negative pressure to allow flow of treated air trapped in the filter 10b into the surrounding i.e. exterior of the system 100. The flow of cold air from the surrounding through the housing 102 provides cooling of the lamp 101 placed inside the housing 102 and at the same time takes the ozone particles generated during illumination of the lamp 101. The air containing ozone particles is then treated through the filter 10b before releasing the air into the surroundings by the exhaust fan 10a.

Once again referring to FIGS. 4-6, the lower portion 30 comprises a chassis 302 having provisions to mount a plurality of wheels 50 in order to facilitate mobility of the system 100. The chassis 302 is preferably manufactured from a sheet metal to provide strength to the system 100. The chassis 302 may also by manufactured from different metal or non-metal alloys having high strength and resistance against temperature. A first electronic lock 30a and a second electronic lock 30b is mounted to the chassis 302 at a front end and at a rear end of the system 100. A fourth controller 30c fitted with a plurality of radio antennas 30d, is fitted to the chassis 302 by fasteners. The radio antennas 30d are provided to facilitate remote operation of the UV disinfection system 100 by using a handheld device. The fourth controller 30c is configured to distribute power supply to respective electronic components of the system 100 and acts a main controller for the system 100.

A power intake plug 30e is provided at the rear end of the system 100. The power intake plug 30e is adapted to receive a power cable coming from an input AC power socket. The power intake plug 30e is in electronic communication with a rectifier 30f The rectifier 30f is configured to convert the input AC power supply to a DC power in order to operate different electronic components fitted to the system 100. A circuit breaker 30g and a plurality of relay modules 30h are also mounted on the chassis 302 at the lower portion 30 of the system 100. In between the circuit breaker 30g and the plurality of relay modules 30h, a plurality of power distribution units 30i are mounted on the chassis 302 of the lower portion 30. Each of the power distribution units 30i are provided to facilitate uniform distribution of power among each electronic component associated with the system 100.

The chassis 302 of the system 100 provides provisions to mount a battery module 30j, the battery module 30j comprises of a battery and a battery charger embedded inside the battery module 30j. The battery module 30j is communicatively connected to the rectifier 30f to receive the DC power in order to facilitate charging of the battery placed inside the battery module 30j. The chassis 302 is further mounted with a fifth controller 30k defined as a dual motor logic controller, since according to an embodiment of the present disclosure two motors are mounted on the system 100 for performing respective tasks. The fifth controller 30k is configured to facilitate and control operation of each and every motor mounted to the system 100. The power supply to individual motors are controlled or regulated by a motor power supply module 30m fixed to the chassis 302 of the system 100. The fourth controller 30c may comprise of at least one Central Processing Unit (CPU) which takes commands from the user and controls all the components within the system 100, including the first controller 10e, second controller 20c, motors, actuators, battery module 30j, plurality of relay modules 30h etc.

Referring to FIGS. 7-10, another embodiment of the UV disinfection system 100 is shown. The UV disinfection system 100 comprises a shutter mechanism to protect the lamp 101 from accidental damages when the system 100 is in "non-operating" condition. The shutter mechanism comprising the at least one shutter 104 configured to extend or retract from the intermediate portion 20 of the system 100 and adapted to isolate the UV lamp 101 from surroundings. The shutter 104 is adapted to receive inside the intermediate casing 201 of the intermediate portion 20 in open position. The open position of the shutter 104 is defined as a position when the shutter 104 is completely retracted and received inside the intermediate casing 201. In other words, the shutter 104 is allowed to be in the open position with the system 100 is in the operating condition. Similarly, the shutter 104 is allowed to be in a closed position when the system 100 is in the non-operating condition. The operation of the shutter mechanism may be controlled by an actuator driven by a power supply. The shutter 104 may connected to different mechanical or electromechanical linkages to facilitate transmission of power from the actuator to the shutter 104, to facilitate opening/closing of the shutter 104. The actuator may utilize a hydraulic, electrical, pneumatic and/or mechanical means to facilitate linear movement of the shutter 104. The plurality of shutters 104 may be attached to the either head portion 10 or intermediate portion 20 in order to cover more than one side of the housing 102. The plurality of shutter may be operated by dedicated actuators or a single actuator facilitating opening/closing operation of the shutters 104.

Figure 9:
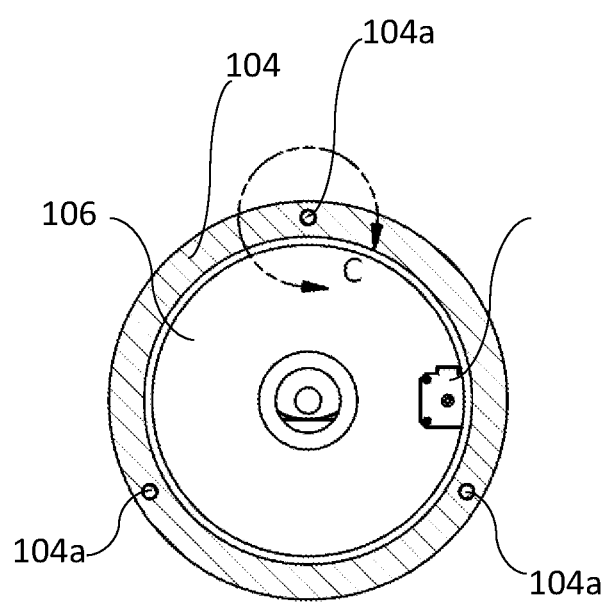
FIG. 9 illustrates a cross-section view along line A-A of the UV disinfection system of FIG. 7.
Figure 10:
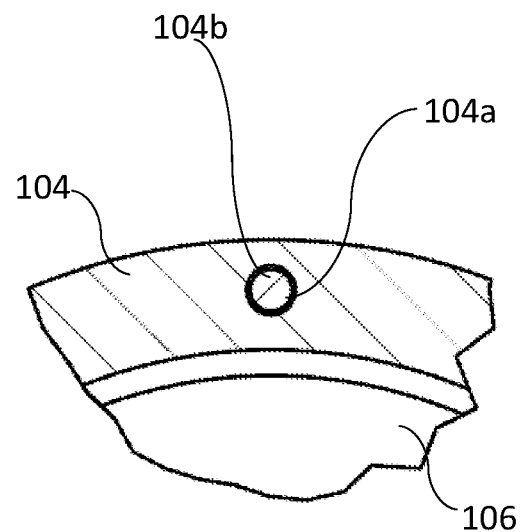
FIG. 10 illustrates an enlarged cross-section view of portion C of FIG. 9.

In an exemplary embodiment of the present disclosure, the shutter 104 is defined with at least two elongated holes 104a, as shown in FIG. 9. The holes 104a are formed on a circumferential surface, in a direction parallel to a vertical axis B-B of the system 100. The vertical axis B-B is defined as an axis passing through center of the intake fan 20a and perpendicular to a horizontal plane of the chassis 302. Each of the at least two elongated holes 104a are adapted to receive at least one ball screw 104b and at least one linear guide rail 104j ball screw. However, lead screws may also be used instead of ball screw to facilitate linear movement of the shutter 104. The at least one ball screw 104b is rotatably mounted on the third plate 203 of the intermediate portion 20. The ball screw 104b may be mounted on the third plate 203 by using bearings to facilitate smooth rotation of the ball screw 104b. However, other mounting means may also be implemented to facilitate mounting of the ball screw 104b on the third plate 203. The at least one ball screw 104b is coupled to a first output shaft of a first motor 104c to facilitate rotation of said ball screw 104b.

The ball screw 104b is defined with a plurality of outer threads which are adapted to engage with a plurality of inner threads formed on a carriage 104i received in the ball screw 104b. The ball screw 104b may further comprise of plurality of balls adapted to move along grooves of the outer threads of the ball screw 104i which are engaged with the inner threads of the carriage 104i. The carriage 104i is configured to have a linear movement along length of the ball screw 104b depending on rotation of the ball screw 104b. The carriage 104i is slidably engaged with the linear guide rail 104j comprising a lubrication or a ball bearing as an intermediate member between the carriage 104i and the linear guide rail 104j. The linear guide rail 104j is positioned parallel to the ball screw 104b. The lubrication or the ball bearing provides smooth sliding movement of the carriage 104i along the linear guide rail 104j during linear movement of the carriage 104i. The shutter 104 is removably connected to the carriage 104i, such that the linear movement of the carriage 104i may get transferred to the shutter 104 in order to facilitate linear movement or reciprocating movement of the shutter 104.

The first motor 104c is communicatively connected to the fourth controller 30c to govern operation of the shutter mechanism. At least two sensors are mounted on two extreme opposite ends of the ball screw 104b to detect extended or retracted position of the shutter 104. The first motor 104c is embedded with encoders to share feedback to the fourth controller 30c regarding the position of shutter 104 during opening/closing of the shutter 104. Once the fourth controller 30c received signal from the user to operate the shutter mechanism, the first motor 104c starts to rotate which in turn rotates one of the ball screw 104b coupled to the first output shaft of the first motor 104c. The rotatory movement of the ball screw 104b facilitates engagement/disengagement between the plurality of outer threads on the ball screw 104b and the plurality of inner threads provided to the carriage 104i, resulting in linear movement of the carriage 104i along the length of the ball screw 104b. The linear movement of the carriage 104i governs reciprocating movement of the shutter 104 along the vertical axis B-B to facilitate opening/closing of the shutter 104. As shown in FIG. 8, the shutter 104 is in the open position i.e. in the complete retracted position.

The system 100 may utilize different shutter mechanism to facilitate opening and/or closing of the shutter 104 of the UV disinfection system 100, during operating and/or non-operating condition of the system 100. Another shutter mechanism for opening and/or closing of the shutter 104 of the system 100 is described below, according to another embodiment of the present disclosure.

In another exemplary embodiment of the present disclosure and referring to FIGS. 11a-12c, the shutter 104 may have a sideways movement or circumferential movement to facilitate opening and/or closing of the shutter 104. The shutter 104 is defined having a semi-cylindrical shaped structure comprising at least two pair of cams 104d, as shown in FIG. 12c. However, the shape and size of the shutter 104 may be varied depending upon size and shape of the head portion 10 of the system 100. Each of the cams 104d are adapted to be received in a circumferential slot 104e on the head portion 10. The circumferential slot 104e may be formed either on the first plate 105 or on the second plate 202 of the system 100. In another embodiment, the circumferential slot 104e may be formed on both of the first plate 105 and the second plate 202 of the system to facilitate smooth rotation of the shutter 104.

The first motor 104c is mounted on the first plate 105 of the head portion 10, as shown in FIGS. 11a-12b. The first motor 104c is rotatably connected to a driving gear 104f which is engaged with a driven gear 104g. The driven gear 104g may defined as a planetary gear and is mounted on the first plate 105 of the head portion 10. The driven gear 104g comprises a radially extending arm 104h, such that a slot on the radially extending arm 104h is aligned with the circumferential slot 104e. One of the cams 104d is adapted to be passed through the slot on the arm 104h and then to be received in the circumferential slot 104e, such that the rotary movement of the driven gear 104g facilitates rotary movement of the shutter 104.

Figures 11A, 11B:
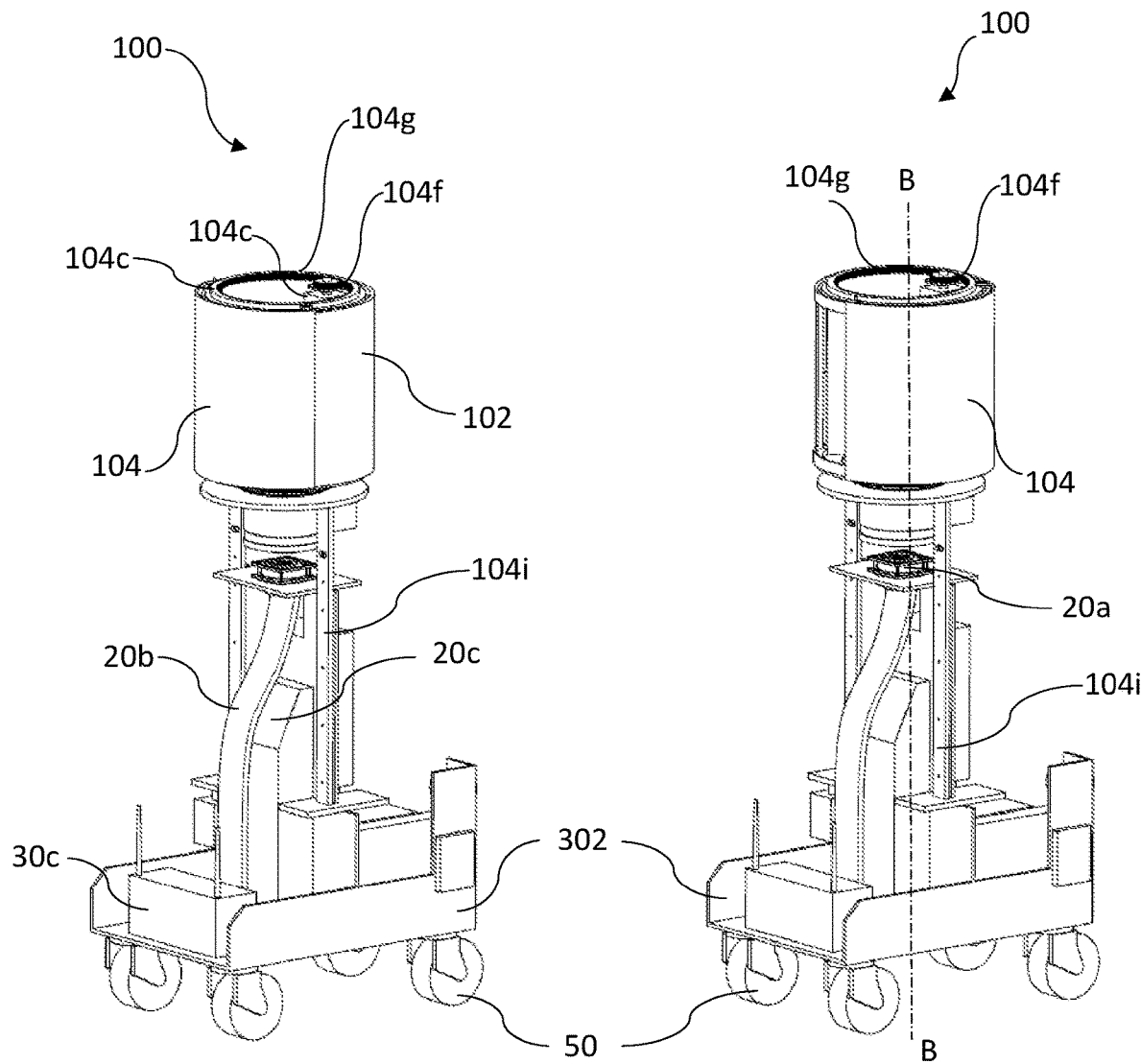
FIG. 11a illustrates front perspective view of the UV disinfection system with closed shutter position, in accordance with an embodiment of the present disclosure.
FIG. 11b illustrates front perspective view of the UV disinfection system with partial open shutter position, in accordance with an embodiment of the present disclosure.

During opening of the shutter 104, the actuation of the first motor 104c facilitates rotation of the driving gear 104f which in turn transmits the rotating force to the driven gear 104g. The transmission of rotating force to the driven gear 104g facilitates rotation of the driven gear 104g. The radially extending arm 104h integrally formed with the driven gear 104g also rotates along the circumferential slot 104e. The arm 104h being connected to the cam 104d exerts a pull force on the shutter 104 along the circumferential slot 104e to facilitate opening of the shutter 104 of the system 100, as shown in FIG. 11b and FIG. 12b. During closing of the shutter 104, the first motor 104c receives an input to get actuated in opposite direction based on the signal transmitted from the fifth controller 30k i.e. dual motor logic controller. The opposite rotation of the first motor 104c results in opposite rotation of the driving gear 104f, the driven gear 104g and the arm 104h, which in turn exerts a push force on the shutter 104 through the cam 104d to facilitate closing of the shutter 104. During opening/closing of the shutter 104, the shutter 104 is configured to oscillate around the vertical axis B-B, along the circumferential slot 104e due to sliding movement of the cams 104d received in the circumferential slot 104e. The shutter 104 is configured to slide in close proximity of the housing 102 during opening of the shutter 104. During opening of the shutter 104, it first comes out clearing the housing 102 and then starts to rotate along the housing 102 depending on rotation of the first motor 104c. The said movement of the shutter 104 is governed by the movement of the cams 104d along the circumferential slot 104e provided on the first plate 105 and/or the second plate 202 of the housing 102.

The reflector 103 located behind the lamp 101 is configured to redirect or reflect the UV rays onto the targeted objects present inside the room. The reflector 103 is mounted inside the housing 102 of the head portion 10 of the system 100, such that it is adapted to move in different directions with respect to the lamp 101. The reflector 103 is connected to different mechanisms to facilitate linear as well as rotational movement of the reflector 103 with respect to the lamp 101 simultaneously. The system 100 comprising the head portion 10 may be fitted with a mechanism to facilitate continuous 360° rotation of the reflector 103 around the lamp 101. The continuous rotation of the reflector 103 facilitates scattering of the UV rays in all directions to cover entire area surrounding the system 100. The continuous 360° rotation of the reflector 103 also increases efficiency of the system 100 and prevents repeated re-positioning of the system 100 for disinfecting of objects or tools placed in a particular location. The continuous 360° rotation of the reflector 103 may be achieved by connecting the reflector 103 to the base plate 106. The base plate 106 may be rotatably coupled to an actuator driven by an input power source to facilitate rotation of the base plate 106.

The reflector 103 may have a parabolic profile, cylindrical profile having an open side, elliptical profile or any other desired shape in accordance with the requirement of treatment. Further, the reflector 103 may be in the form of a single part such as a single molded unit or a combination of multiple parts or sections joined together to form a desired profile. Further, the shape of the reflector 103 can be varied based on the treatment conditions. The reflector 103 may be manufactured from a thin flexible material adapted to reflect the UV rays emitted by the lamp 101. The flexible material may be defined as a sheet metal, composite materials, alloys or likewise having a reflecting surface adapted to reflected UV rays emitted by the lamp 101 into the surroundings.

In an exemplary embodiment and referring to FIGS. 13-15c, the reflector 103 is connected to the frame 107 covering a non-reflecting surface of the reflector 103. The reflector 103 is rigidly fixed to the frame 107 by using rivets or other mechanical joining means. The frame 107 comprises a first flange 107a and a pair of second flanges 107b to facilitate mounting of the frame 107 on the base plate 106. The first flange 107a extends from a bottom edge of a rear wall of the frame 107 in a direction away from the lamp 101. The pair of second flanges 107b extend from bottom edge of side walls of the frame 107 towards the lamp 101, as shown in FIGS. 15a-15c. Each flange of the pair of second flanges 107b comprises a plurality of guiding knobs 107c.

The base plate 106 comprises a hole 106a adapted to receive a socket 101a for connecting the at least one lamp 101. The socket 101a is connected to the power source by a plurality of wires to facilitate transmission of current from the power source to the lamp 101. The hole 106a prevents direct contact of the lamp 101 or socket 101a with the base plate 106. The hole 106a is provided to allow the independent mounting of the lamp 101 with the intermediate portion 20 of the system 100. The hole 106a prevents movement of the lamp 101 with respect to the reflector 103 and makes the lamp 101 stand still inside the housing 102 during operating condition. According to an exemplary embodiment, the hole 106a is preferably provided at center of the base plate 106. However, the positioning of the hole 106a may vary depending upon positioning of the lamp 101 inside the housing 102. The base plate 106 is mounted with at least two blocks 106b on an upper surface of the base plate 106. In another embodiment of present disclosure, one linear block may be utilized to facilitate linear movement of the reflector. Each of the at least two blocks 106b are provided with a longitudinal slot 106c adapted to receive the plurality of guiding knobs 107c of the frame 107. The reflector 103 fixed to the frame 107 is attached to the base plate 106 through the plurality of guiding knobs 107c received in the slot 106c formed on the blocks 106b of the base plate 106.

In an embodiment of the present disclosure, a mechanism to facilitate rotational movement of the reflector 103 is disclosed. The head portion 10 of the system 100 comprises a second motor 106d to facilitate continuous 360° rotation of the reflector 103. The second motor 106d provided with a toothed second output shaft 106e configured to engage with a plurality of teeth 106f formed on circumference of the base plate 106. The actuation of the second motor 106d is achieved by the signals transmitted from the fourth controller 30c depending upon the user input. The user provide command to the fourth controller 30c or the system 100 (in general) either by a wireless handheld device or by a touch panel mounted on the system 100 itself. The actuation of the second motor 106d transmits the rotating movement from the second motor 106d to the base plate 106. The rotating movement transmitted to the base plate 106 facilitates rotation of the base plate 106 and the frame 107 connected to the base plate 106. The reflector 103 being fixed to the frame 107 also possess the rotating movement simultaneously with rotation of the base plate 106. The rotation of base plate 106 due to actuation of the second motor 106d facilitates continuous 360° of the reflector 103, which in turn reflects the UV rays emitted by the lamp 101 in all directions around the system 100. The rotation speed of the reflector 103 may be controlled manually or automatically based on room conditions. The rotational movement of the reflector 103 do not result in twisting or tangling of wires connected to the lamp 101 through socket 101a.

Further, the continuous rotation of the reflector 103 facilitates dispersion of UV rays uniformly in all directions and prevents the tiresome task for the user of relocating the system 100 to treat objects placed in remote locations.

However, different other mechanisms may be utilized to facilitate rotational movement of the reflector. One such mechanism may comprise of a chain-pulley system to achieve the similar functions and to facilitate rotational movement of the reflector. The chain-pulley system may comprise of a base plate having external pulley teeth being engaged with the teeth on actuator shaft by an engaging belt having internal teeth. A worm gear drive mechanism may be utilized, and similarly other relevant mechanisms may be utilized to achieve the same functions to facilitate rotational movement to the reflector 103.

In an embodiment of the present disclosure, a mechanism to facilitate linear movement of the reflector 103 is disclosed. The base plate 106 is formed with a platform 106g protruding from the upper surface of the base plate 106. The platform 106g is formed facing the rear surface of the frame 107 and said platform 106g is adapted to receive a first actuator 60. The first actuator 60 is defined as a linear actuator for example—hydraulic actuator, pneumatic actuator, semi-hydraulic actuator, electrical actuator and/or electromechanical actuator etc but not limited to the same. The first actuator 60 comprises a first drive shaft 60a configured to connect the first actuator 60 with the first flange 107a extending from the frame 107. The first drive shaft 60a is configured to extend or retract depending upon the actuation of the first actuator 60. The first actuator 60 is provided to vary position of the reflector 103 fixed to the frame 107 with respect to the lamp 101.

Once the first actuator 60 receives signal from the user, the first drive shaft 60a extends/retracts to linearly vary the position of reflector 103 from the lamp 101. The linear movement of the first drive shaft 60a exerts push/pull force on the frame 107, which in turn results in sliding movement of the frame 107 over the at least two blocks 106b provided on the base plate 106 of the system 100. The sliding movement of the frame 107 results in simultaneous linear movement of the reflector 103 being fixed the frame 107.

Referring to FIGS. 15(a) to 15(c), various position of the reflector 103 is shown in accordance with the present disclosure. The position of light source with respect to the focal point governs the scattering/dispersion of light rays after getting reflected from reflecting surface of the reflector 103. FIG. 15(a) illustrates the reflector 103 positioned linearly at focal point to facilitate uniform and parallel dispersion of the reflected UV rays. FIG. 15(b) shows the reflector 103 positioned linearly away from focal point to converge the reflected UV rays to treat objects placed at closer locations in the room. FIG. 15(c) illustrates the reflector 103 positioned before the focal point to facilitate dispersion of reflected UV rays at greater angles in order to treat the larger region of the surrounding/room. The light coverage can be changed dynamically by changing relative position of the reflector 103 with respect to the lamp 101 by operating the first actuator 60.

In an embodiment of the present disclosure, the reflector 103 can change its shape based on the kind of application for which the UV disinfection system 100 is used. The reflector 103 is made up of a thin metal sheet or other reflecting material having high reflectance preferably greater than 50% reflectance to ultraviolet light, or more specifically, greater than 80% reflectance to ultraviolet light and/or visible violet-blue light. The thin sheet of reflector 103 may be connected to plurality of actuators to facilitate shape changing of the reflector 103. The shape of the reflector 103 is varied in order to converge or diverge the UV rays in accordance with the treatment required like to target specific regions for example: bed handrails, handles etc. The actuator responsible for varying shape of the reflector 103 may be connected to fourth controller 30c configured to receive input data with respect to the desired shape of the reflector 103. The user may feed the data based upon the area to be treated and other physical characteristics of the room. The actuator can utilize hydraulic and/or mechanical and/or electrical and/or electromechanical means to facilitate dynamic shape changing of the reflector 103. The dynamic shape changing of the reflector 103 may also be achieved by plurality of actuators exerting precise force at different locations of the reflector 103. The force is exerted by the actuators is responsible to change the shape of reflector 103 for example, from parabolic shape to elliptical shape or to other configurations.

Referring to FIG. 16-20c, in accordance with an embodiment, a mechanism to facilitate changing the shape of the reflector 103 is shown. The mechanism to change the shape of the reflector 103 comprises a second actuator 70 having a second drive shaft 70a to facilitate change in shape of the reflector 103. The shape changing mechanism further comprises a pair of internal arms 70b, a pair of external arms 70c, a first bracket 70d, a second bracket 70e, such that the first bracket 70d and the second bracket 70e are connected to each other by the second actuator 70. The pair of internal arms 70b are pivotably connected to the reflector 103 through the first bracket 70d and the pair of external arms 70c are pivotably connected to the reflector 103 through the second bracket 70e. The second bracket 70e is connected to the second actuator 70 through the second drive shaft 70a to facilitate changing of shape of the reflector 103.

The second actuator 70 comprising a proximal end and a distal end, such that the driving shaft 70a is located at the distal end of the actuator 70. The 'proximal end' herein refers to an end of the actuator 70 in proximity to the reflector 103; the 'distal end' herein refers to an end located away from the proximal end. The driving shaft 70a is adapted to extend and retract by hydraulic, pneumatic or electro mechanic means or any other mechanical means. The driving shaft 70a having an open end is attached to the second bracket 70e while the first bracket 70d is fixed at proximal end of the actuator 70 supporting the reflector 103. The first bracket 70d is defined having a wedge-shaped flange 70f provided at center of the first bracket 70d to provide support to the reflector 103. The external arms 70c are pivotably connected to the second bracket 70e at one end and pivotably connected to the reflector 103 at other end. The internal arms 70b are pivotably connected to the first bracket 70d at one end and pivotably connected to the reflector 103 at other end.

The second actuator 70 is configured to govern linear movement of the second drive shaft 70a to facilitate pivotal movement of the external arms 70c in order to change shape of the reflector 103. The linear movement of the second drive shaft 70a exerts a push/pull force on the external arms 70c to bend the reflector 103 is a desired shape. The first bracket 70d and the pair of internal arms 70b provides extra strength and support to the reflector 103 preventing damaging of the reflector 103 during changing shape of the reflector 103. The first actuator 60 and the second actuator 70 may be defined as linear actuators and may utilize any hydraulic, pneumatic, mechanical, electro-mechanical means to facilitate linear movement of the respective drive shafts 60a, 70a. The shape changing mechanism is removably attached to the reflector 103 by means of mechanical fasteners and is supported by the frame 107.

In another embodiment of the present disclosure, the shape changing mechanism may be supported by a vertical beam. The vertical beam having one end may be rigidly fixed to the base plate and the other end may be removably connected to the actuator 70. The vertical beam may provide additional support to the actuator 70 and provides a compact assembly to the shape changing mechanism. Other supporting structures may also be utilized to provide proper support to the shape changing mechanism and to easier the assembling process.

In an embodiment of the present disclosure, the working of shape changing mechanism for a reflector 103 is disclosed. In operating condition, the second actuator 70 receives a command from the fourth controller 30c to change shape of the reflector 103 in order to facilitate treatment of identified targeted surfaces. The second actuator 70 provides linear movement to the second drive shaft 70a such that the second drive shaft 70a extends linearly away from the reflector 103 to a predetermined length. The linear movement of the second drive shaft 70a being attached with the second bracket 70e facilitates pivotal movement of the external arms 70c. The pivotal movement of the external arms 70c apply pulling force to the reflector 103 to facilitate change in shape/profile of the reflector 103. The rear surface of reflector 103 being in contact with the curved wedge-shaped flange 70f of the first bracket 70d provides support to the reflector 103 and prevents any accidental damage to the reflector 103 during operating condition. The variation in shape or profile of reflector 103 depends upon the extended or retracted length of the second drive shaft 70a which is governed by the fourth controller 30c or manually by the user.

Referring to FIGS. 20(a)-20(c), three different positions of the second drive shaft 70a is shown in order to facilitate change in shape of the reflector 103. FIG. 20(a) shows a retracted position of the second drive shaft 70c keeping the initial shape of the reflector 103. FIG. 20(b) shows an intermediate position in which the second drive shaft 70c is in partially extended position such that the shape of the reflector 103 is changed to partially open configuration. FIG. 20(c) illustrates a completely extended position of the second drive shaft 70c such that shape of the reflector 103 is changed to completely open configuration to facilitate maximum divergence of the reflected UV rays. In an embodiment, there can be multiple intermediate positions, in which the second drive shaft 70c may actuate from completely retracted position to completely extended position based on the commands received from the fourth controller 30c or manually from the user.

In an embodiment of the present disclosure, the reflector 103 may also be formed from an array of small square, rectangular or other polygonal shaped reflectors connected together to form a desired profile of the reflector 103. Each polygonal shaped reflector is connected to a dedicated actuator 70 to facilitate linear and/or rotational movement of said reflector independently in order to change direction of reflected rays. Also, the reflector 103 may be formed by stacking smaller profiles on top of each other, each profile being independently actuated by its own actuator 70 to facilitate change in shape of the specific profile of the reflector 103. In an embodiment, a camera may be mounted on head portion 10 of the UV disinfection system 100 to provide information about type of surface on which the UV rays are falling. The camera may also detect the hard to reach surfaces and transmit the information to the fourth controller 30c or the third controller 20d. The respective controller process the information and commands the dedicated actuator to change the position of one section of the reflector 103. The variation in position of the section of the reflector 103 facilitates projection of reflected UV rays onto the detected hard to reach surface. Different kind of sensors may be utilized apart from camera to provide the same functionality and to improve the treatment process.

The UV disinfection system 100 comprises a user interface which helps the user to feed data into the system 100 in order to perform different functions. In an embodiment, the actuators may be manually operated to perform desired function. Further, the UV disinfection system 100 may comprise plurality of sensors to monitor and gather information related to the treatment process and/or physical characteristics of the room in which the system 100 is placed and send data to the respective controllers. The controllers are configured to process the data and generate output to operate the actuators to perform respective functions automatically in order to provide effective and efficient treatment of the objects present in the room and/or surrounding the system 100. The controller facilitates the treatment process with minimum human intervention and with maximum efficiency.

The UV disinfection system in accordance with the present disclosure provides continuous pulsed UV rays to disinfect/decontaminate objects present inside a room and/or surrounding the system. The extendable head portion of the UV disinfection system allows treatment of objects present at different heights. The shutter mechanism provided on lower portion of the system provides dedicated protection to the head portion and preferably to the lamp placed inside the head portion from accidental damages. Further, the relative movement of reflector with respect to the lamp facilitates uniform and desired dispersion of UV rays emitted by the lamp. The treatment process is further improved by using shape changing mechanism for the reflector to converge or diverge UV rays based upon the requirement of the treatment process. The UV disinfection machine comprises different controllers to process the data and information received from the user and/or from the sensors to precisely perform treatment process and with maximum efficiency.

EQUIVALENTS

The embodiments herein and the various features and advantageous details thereof are explained with reference to the non-limiting embodiments in the description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

| Reference Numerals: | |
|---|---|
| UV disinfection system | 100 |
| Head portion | 10 |
| Exhaust fan | 10a |
| Filter | 10b |
| First mesh plate | 10c |
| Second mesh plate | 10d |
| First controller | 10e |
| Exhaust air grill | 10f |
| Lamp | 101 |
| Socket | 101a |
| Housing | 102 |
| Window | 1021 |
| Reflector | 103 |
| Shutter | 104 |
| Holes | 104a |
| Ball screw | 104b |
| First motor | 104c |
| Cams | 104d |
| Circumferential slot | 104e |
| Driving gear | 104f |
| Driven gear | 104g |
| Arm | 104h |
| Carriage | 104i |
| Linear guide rail | 104j |
| First plate | 105 |
| Base plate | 106 |
| Hole on base plate | 106a |
| Blocks | 106b |
| Longitudinal slot | 106c |
| Second motor | 106d |
| Toothed second output shaft | 106e |
| Plurality of teeth on base plate | 106f |
| Platform | 106g |

-continued

| Reference Numerals: | |
|---|---|
| Frame | 107 |
| First flange | 107a |
| Pair of second flange | 107b |
| Plurality of guiding knobs | 107c |
| Intermediate portion | 20 |
| Intake fan | 20a |
| Conduit | 20b |
| Second controller | 20c |
| Third controller | 20d |
| Intermediate casing | 201 |
| Second plate | 202 |
| Third plate | 203 |
| Lower portion | 30 |
| Lower casing | 301 |
| Chassis | 302 |
| First electronic lock | 30a |
| Second electronic lock | 30b |
| Fourth controller | 30c |
| Radio antennas | 30d |
| Power intake plug | 30e |
| Rectifier | 30f |
| Circuit breaker | 30g |
| Relay modules | 30h |
| Power distribution units | 30i |
| Battery module | 30j |
| Fifth controller | 30k |
| Motor power supply module | 30m |
| Handle | 40 |
| Wheels | 50 |
| First actuator | 60 |
| First drive shaft | 60a |
| Second actuator | 70 |
| Second drive shaft | 70a |
| Pair of internal arms | 70b |
| Pair of external arms | 70c |
| First bracket | 70d |
| Second bracket | 70e |
| Wedge-shaped flange | 70f |

We claim:

1. A ultraviolet (UV) disinfection system, the system comprising:
   a head portion mounted on an intermediate portion of the UV disinfection system, wherein the head portion comprises:
   at least one UV lamp;
   a shutter mechanism comprising a shutter adapted to isolate the UV lamp from surroundings, wherein the shutter is defined with at least two elongated holes configured to receive at one ball screw and at least one linear guide rail;
   wherein, the at least one ball screw is coupled with a first output shaft of a first motor to facilitate reciprocating movement of the shutter.

2. The UV disinfection system as claimed in claim 1, wherein the UV disinfection system comprises at least one reflector positioned around the at least one UV lamp and the at least one reflector is configured to direct UV rays emitted from the UV lamp to the surroundings.

3. The UV disinfection system as claimed in claim 1, wherein a carriage is engaged with the at least one ball screw and the at least one linear guide rail, the carriage comprising:
   a plurality of inner threads adapted to engage with a plurality of outer threads formed on the ball screw to facilitate linear movement of the carriage along a length of the ball screw.

4. The UV disinfection system as claimed in claim 1, wherein the carriage is removably connected to the shutter, such that the linear movement of the carriage is transmitted to the shutter to facilitate reciprocating movement of the shutter.

5. The UV disinfection system as claimed in claim 1, wherein the first motor is communicatively connected to a processor configured to govern operation of the shutter mechanism by causing the first motor to rotate upon receipt of an operation signal from a user.

6. The UV disinfection system as claimed in claim 1, wherein the intermediate portion comprises a plate, wherein the plate provides provisions for rotatably connecting the at least one ball screw and the at least one linear guide rail to the plate.

7. The UV disinfection system as claimed in claim 1, wherein the shutter comprises at least two pair of cams adapted to be received in a circumferential slot formed on the head portion.

8. A ultraviolet (UV) disinfection system, the system comprising:
   a head portion mounted on an intermediate portion of the UV disinfection system, wherein the head portion comprises:
   at least one UV lamp;
   at least one reflector configured to direct UV rays emitted from the at least one UV lamp, wherein
   the at least one reflector is connected to a frame;
   the frame is connected to a first drive shaft of a first actuator, and wherein
   the first actuator facilitates linear movement of the at least one reflector connected to the frame to vary reflection pattern of the UV rays.

9. The UV disinfection system as claimed in claim 8, wherein the frame comprises:
   a first flange and a pair of second flanges, wherein
   the first flange extends from a rear wall of the frame to connect the first drive shaft with the frame, and
   each flange of the pair of second flanges comprises a plurality of guiding knobs.

10. The UV disinfection system as claimed in claim 8, wherein the head portion comprises a base plate, wherein the base plate comprises:
    a hole, and
    a plurality of teeth formed along a circumference of the base plate.

11. The UV disinfection system as claimed in claim 8, wherein the hole is provided on the base plate to receive a socket for connecting the at least one UV lamp.

12. The UV disinfection system as claimed in claim 8, wherein at least two blocks are mounted on an upper surface of the base plate, wherein
    each of the at least two blocks are provided with a slot adapted to receive the plurality of guiding knobs, to facilitate linear movement of the reflector fixed with the frame.

13. The UV disinfection system as claimed in claim 12, wherein a plurality of teeth on the base plate are configured to engage with a plurality of teeth formed on a second output shaft of a second motor to facilitate oscillation of the reflector connected to the base plate.

14. A ultraviolet (UV) disinfection system, the system comprising:
    a head portion mounted on an intermediate portion of the UV disinfection system, wherein the head portion comprises:

at least one UV lamp;

a reflector configured to direct UV rays from the at least one UV lamp, wherein the reflector is connected to a shape changing mechanism, wherein the mechanism comprises:

a pair of internal arms pivotably connected to the reflector through a first bracket;

a pair of external arms pivotably connected to the reflector through a second bracket;

wherein the first bracket and the second bracket are connected to each other an actuator, and wherein the second bracket is connected to the actuator through a drive shaft to facilitate changing of shape of the reflector.

15. The UV disinfection system as claimed in claim 14, wherein the first bracket is defined with a wedge-shaped flange provided at center of the first bracket to provide support to the reflector.

16. The UV disinfection system as claimed in claim 14, wherein the reflector is manufactured from a flexible material configured to reflect the UV rays emitted by the at least one UV lamp.

17. The UV disinfection system as claimed in claim 14, wherein the actuator is configured to govern linear movement of the second drive shaft to facilitate pivotal movement of the external arms in order to change shape of the reflector.

18. The UV disinfection system as claimed in claim 14, wherein the at least one UV lamp is a pulsed xenon UV lamp.

19. The UV disinfection system as claimed in claim 14, wherein the actuator is a linear actuator.

20. The UV disinfection system as claimed in claim 14, wherein the system comprises a lower portion configured to mount a plurality of wheels to facilitate mobility of the UV disinfection system.

* * * * *